United States Patent
Aharoni et al.

(10) Patent No.: US 10,201,415 B2
(45) Date of Patent: Feb. 12, 2019

(54) METHOD AND APPARATUS FOR PREPARATION AND INSERTION OF AN INTRAOCULAR LENS INTO THE EYE OF A PATIENT

(71) Applicant: Visioncare Ophthalmic Technologies Inc., Saratoga, CA (US)

(72) Inventors: Eli Aharoni, Tel Aviv (IL); Vladimir Belousov, Tsur Itzhak (IL)

(73) Assignee: VISIONCARE, INC., Saratoga, CA (US)

( * ) Notice: Subject to any disclaimer, the term of this patent is extended or adjusted under 35 U.S.C. 154(b) by 218 days.

(21) Appl. No.: 15/030,803

(22) PCT Filed: Nov. 3, 2014

(86) PCT No.: PCT/IL2014/050955
§ 371 (c)(1),
(2) Date: Apr. 20, 2016

(87) PCT Pub. No.: WO2015/063778
PCT Pub. Date: May 7, 2015

(65) Prior Publication Data
US 2016/0278913 A1    Sep. 29, 2016

Related U.S. Application Data

(63) Continuation-in-part of application No. 14/070,958, filed on Nov. 4, 2013, now Pat. No. 9,358,102.
(Continued)

(51) Int. Cl.
*A61F 2/16* (2006.01)
*A61F 9/007* (2006.01)
*A61F 9/00* (2006.01)

(52) U.S. Cl.
CPC .......... *A61F 2/1664* (2013.01); *A61F 2/1691* (2013.01); *A61F 9/007* (2013.01);
(Continued)

(58) Field of Classification Search
CPC ........ A61F 9/007; A61F 9/009; A61F 9/0017; A61F 9/013; A61F 9/0133; A61F 9/0136;
(Continued)

(56) References Cited

U.S. PATENT DOCUMENTS 4,041,552 A    8/1977  Ganias
4,136,406 A    1/1979  Norris
(Continued)

FOREIGN PATENT DOCUMENTS

GB    2242835 A  * 10/1991 ............. A61F 9/013
JP    2007-007332      1/2007
(Continued)

OTHER PUBLICATIONS

Notice of Allowance dated Feb. 9, 2016, issued during the prosecution of U.S. Appl. No. 14/070,958.
(Continued)

*Primary Examiner* — Jonathan Miles
*Assistant Examiner* — Kankindi Rwego
(74) *Attorney, Agent, or Firm* — Locke Lord LLP; Joshua L. Jones

(57) ABSTRACT

Apparatus for guiding surgical formation of a pair of symmetrical sclerectomies in an eye of a patient, including a multi-diameter generally circular cutout portion including at least a first and second portions having corresponding first and second diameters, the cutout portion being arranged for placement over the limbus of the eye and for centering the limbus within one of the first and second portions, thereby enabling estimating the diameter of the limbus, and at least first and second series of sclerectomy guiding apertures
(Continued)

formed about the cutout portion, each guiding aperture of the first series having a paired guiding aperture in the second series formed 180° thereapart relative to a center of the cutout portion, the at least first and second series of sclerectomy guiding apertures together including at least one pair of guiding apertures having a diameter therebetween which is wider than at least one of the first and second portions.

21 Claims, 28 Drawing Sheets

Related U.S. Application Data

(60) Provisional application No. 62/031,255, filed on Jul. 31, 2014.

(52) U.S. Cl.
CPC .... *A61F 9/0017* (2013.01); *A61F 2002/1683* (2013.01); *A61F 2210/0057* (2013.01); *A61F 2220/0033* (2013.01)

(58) Field of Classification Search
CPC .... A61F 2009/00865; A61F 2009/0087; A61F 9/00736; A61F 9/00754; A61F 9/00812; A61F 9/00819; A61F 9/00834; A61F 9/00836; A61F 9/00838; A61F 2009/00872; A61F 2009/00876; A61F 2009/00887; A61F 2009/00895
See application file for complete search history.

(56) References Cited

U.S. PATENT DOCUMENTS

| | | | |
|---|---|---|---|
| 4,190,049 A | 2/1980 | Hager et al. | |
| 4,214,585 A | 7/1980 | Bailey, Jr. | |
| 4,327,450 A | 5/1982 | Girard | |
| 4,657,547 A | 4/1987 | Maggi | |
| 4,662,882 A | 5/1987 | Hoffer | |
| 4,750,904 A | 6/1988 | Price, Jr. | |
| 4,753,655 A | 6/1988 | Hecht | |
| 4,993,128 A | 2/1991 | Gold | |
| 5,006,123 A * | 4/1991 | Soll | A61F 9/007 33/512 |
| 5,336,262 A | 8/1994 | Chu | |
| 5,383,259 A | 1/1995 | McIntire | |
| 5,480,426 A | 1/1996 | Chu | |
| 5,814,103 A | 9/1998 | Lipshitz et al. | |
| 6,152,959 A | 11/2000 | Portney | |
| 6,193,750 B1 | 2/2001 | Cumming | |
| 6,352,542 B1 | 3/2002 | Snyder | |
| 6,443,984 B1 | 9/2002 | Jahn et al. | |
| 7,175,661 B1 | 2/2007 | Chung et al. | |
| 9,358,102 B2 | 6/2016 | Aharoni | |
| 2002/0091442 A1 | 7/2002 | Snyder | |
| 2004/0111152 A1 | 6/2004 | Kelman | |
| 2005/0288785 A1 | 12/2005 | Portney et al. | |
| 2006/0235428 A1* | 10/2006 | Silvestrini | A61F 2/145 606/107 |
| 2007/0027541 A1 | 2/2007 | Aharoni et al. | |
| 2008/0221657 A1 | 9/2008 | Laroya et al. | |
| 2009/0062912 A1 | 3/2009 | Rombach | |
| 2012/0330415 A1 | 12/2012 | Callahan et al. | |
| 2013/0238091 A1 | 9/2013 | Danta et al. | |
| 2014/0371852 A1 | 12/2014 | Aharoni et al. | |
| 2015/0127014 A1 | 5/2015 | Aharoni | |
| 2016/0262877 A1 | 9/2016 | Aharoni | |

FOREIGN PATENT DOCUMENTS

| | | | | |
|---|---|---|---|---|
| WO | WO 2011021225 A1 * | 2/2011 | ........... | A61F 9/0133 |
| WO | WO-2015/063778 A2 | 5/2015 | | |

OTHER PUBLICATIONS

Office Action dated Jun. 16, 2015, issued during the prosecution of U.S. Appl. No. 14/070,958.
Office Action dated May 29, 2015, issued during the prosecution of U.S. Appl. No. 14/070,958.
International Search Report and Written Opinion dated Sep. 18, 2015, issued during the prosecution of International Application No. PCT/IL2014/050955.
International Preliminary Report on Patentability dated May 10, 2016, issued during the prosecution of International Patent Application No. PCT/IL2014/050955.
U.S. Appl. No. 62/031,255, filed Jul. 31, 2014.
Partial Supplementary European Search Report dated Feb. 23, 2017, issued during the prosecution of European Patent Application No. 14858035.0 (6 pages).
An Office Action dated May 24, 2018, which issued during the prosecution of U.S. Appl. No. 15/145,189.
Japanese Office Action and English Translation thereof dated Jul. 24, 2018 which issued during the prosecution of Japanese Patent Application No. 2016-551109.

* cited by examiner

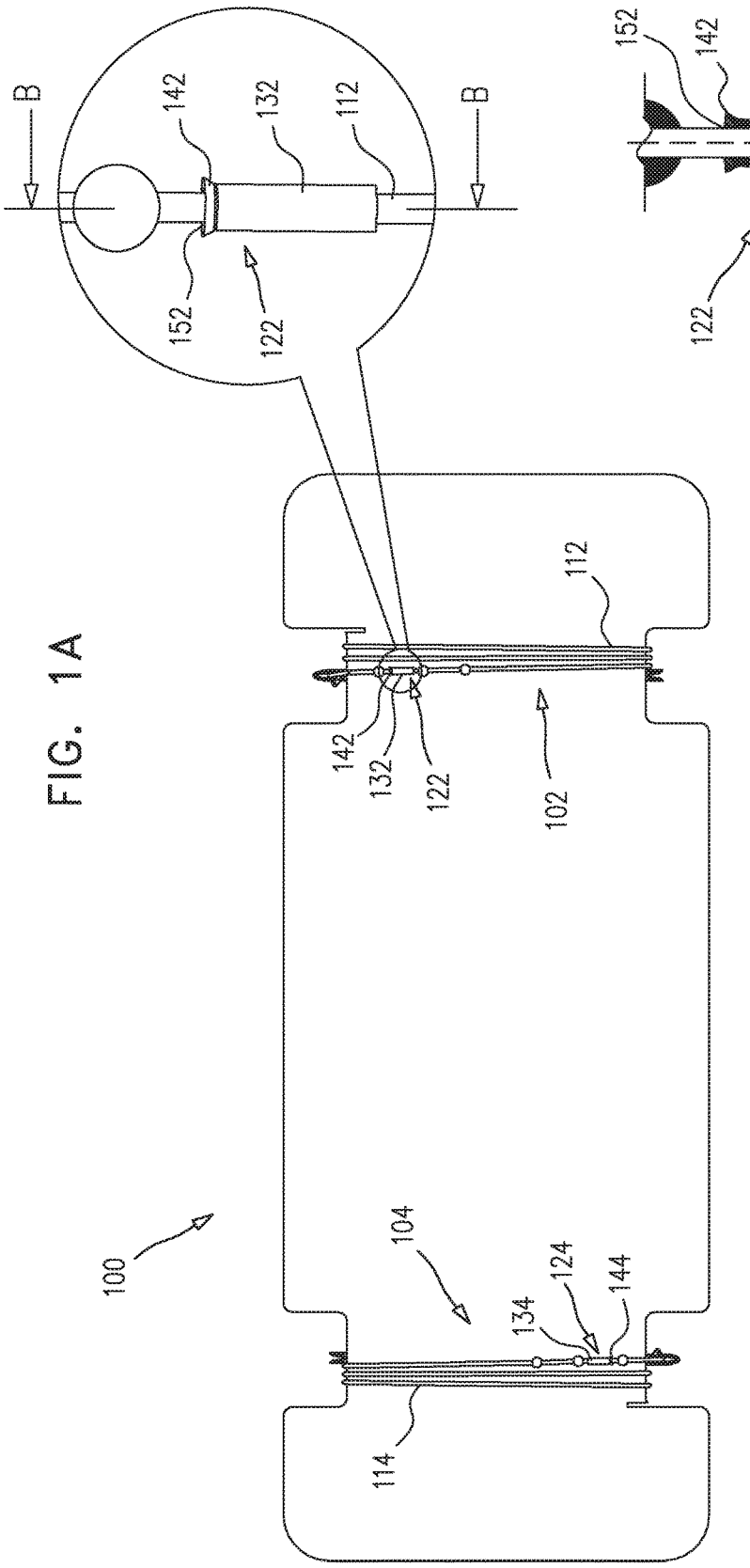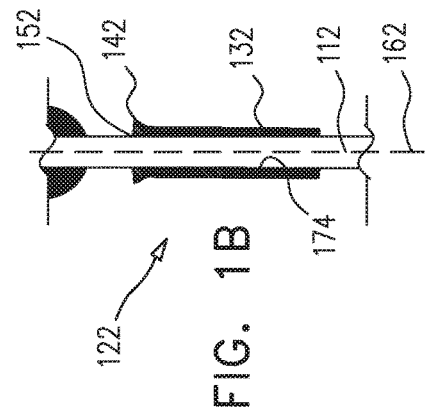

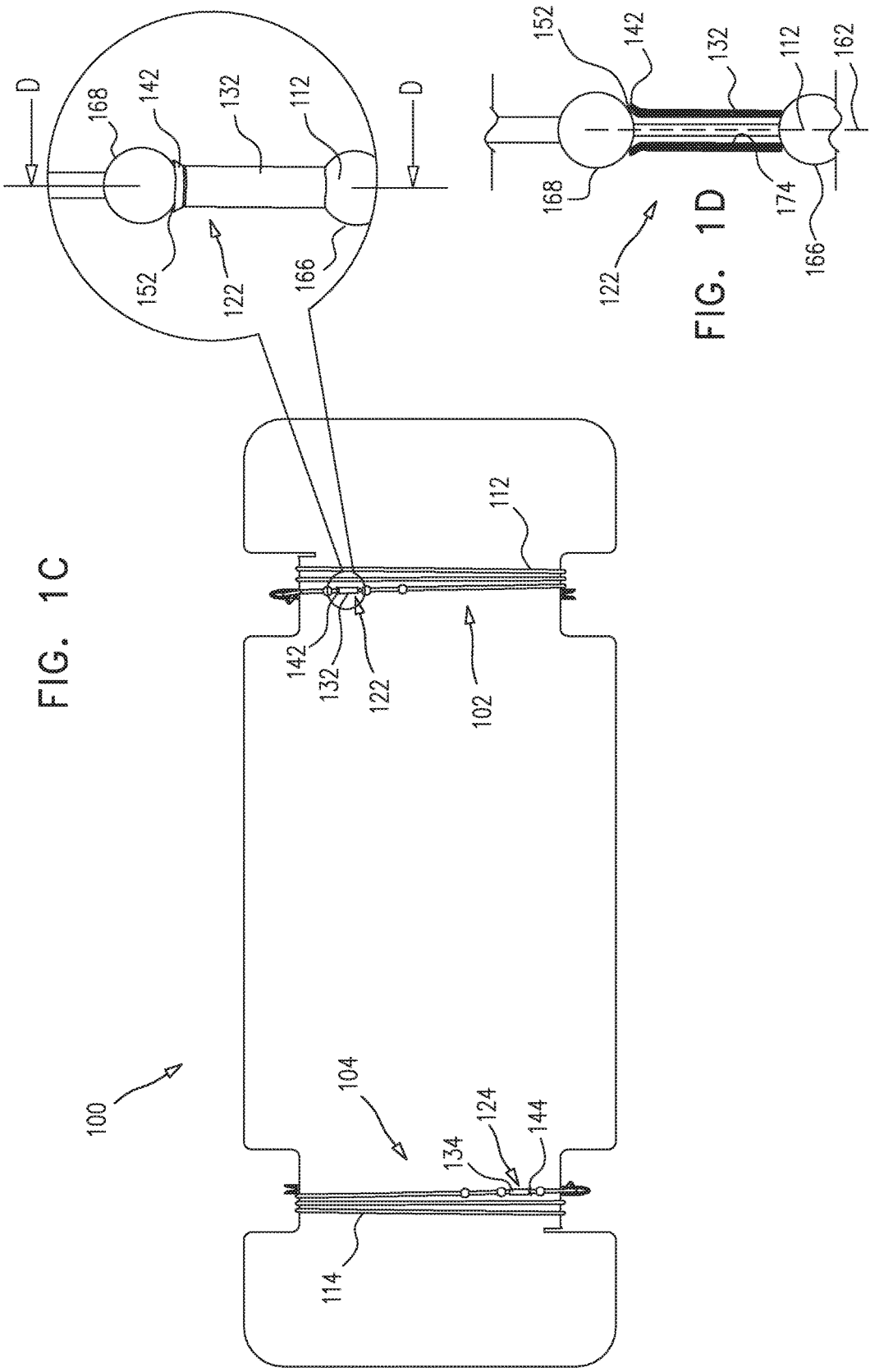

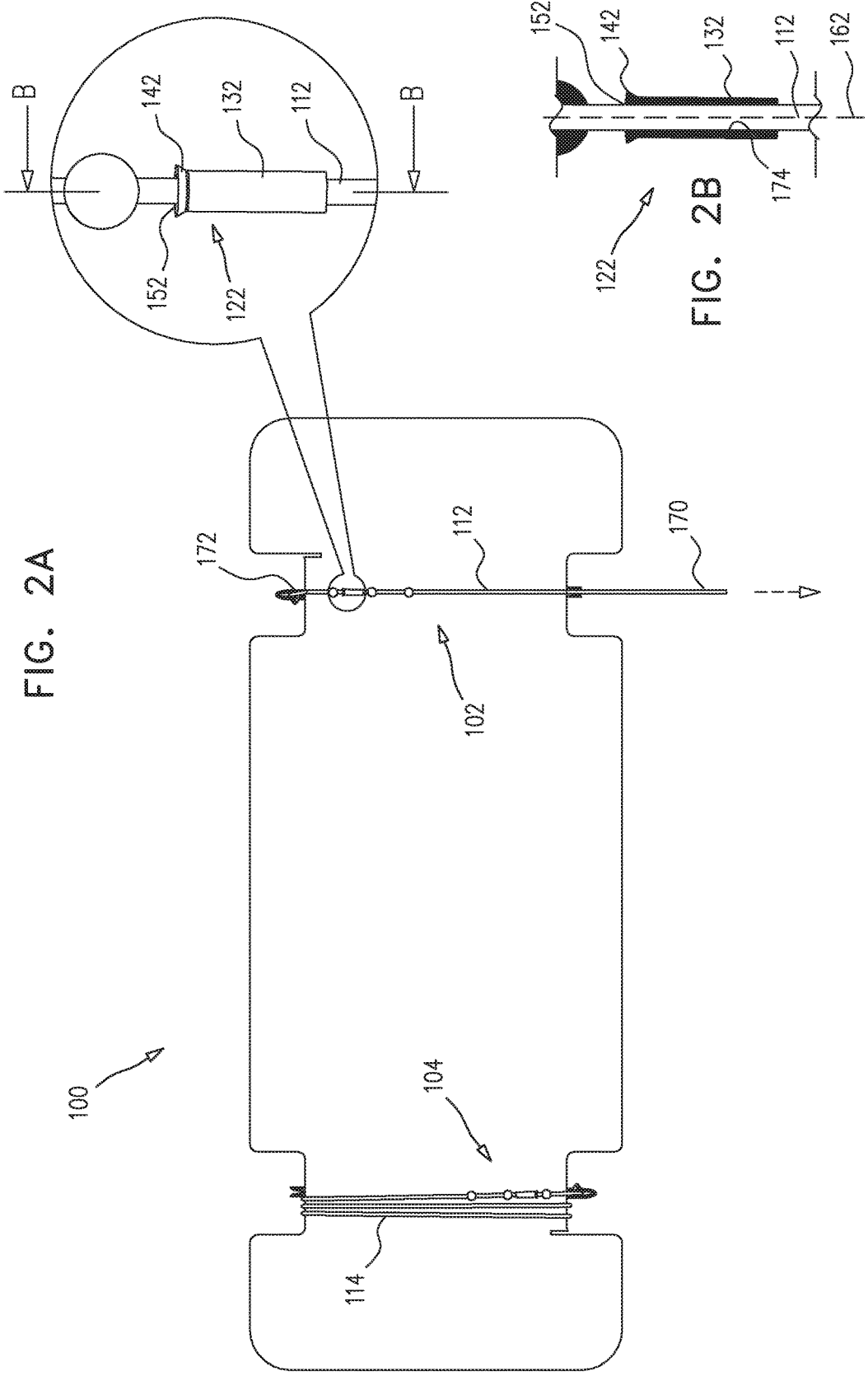

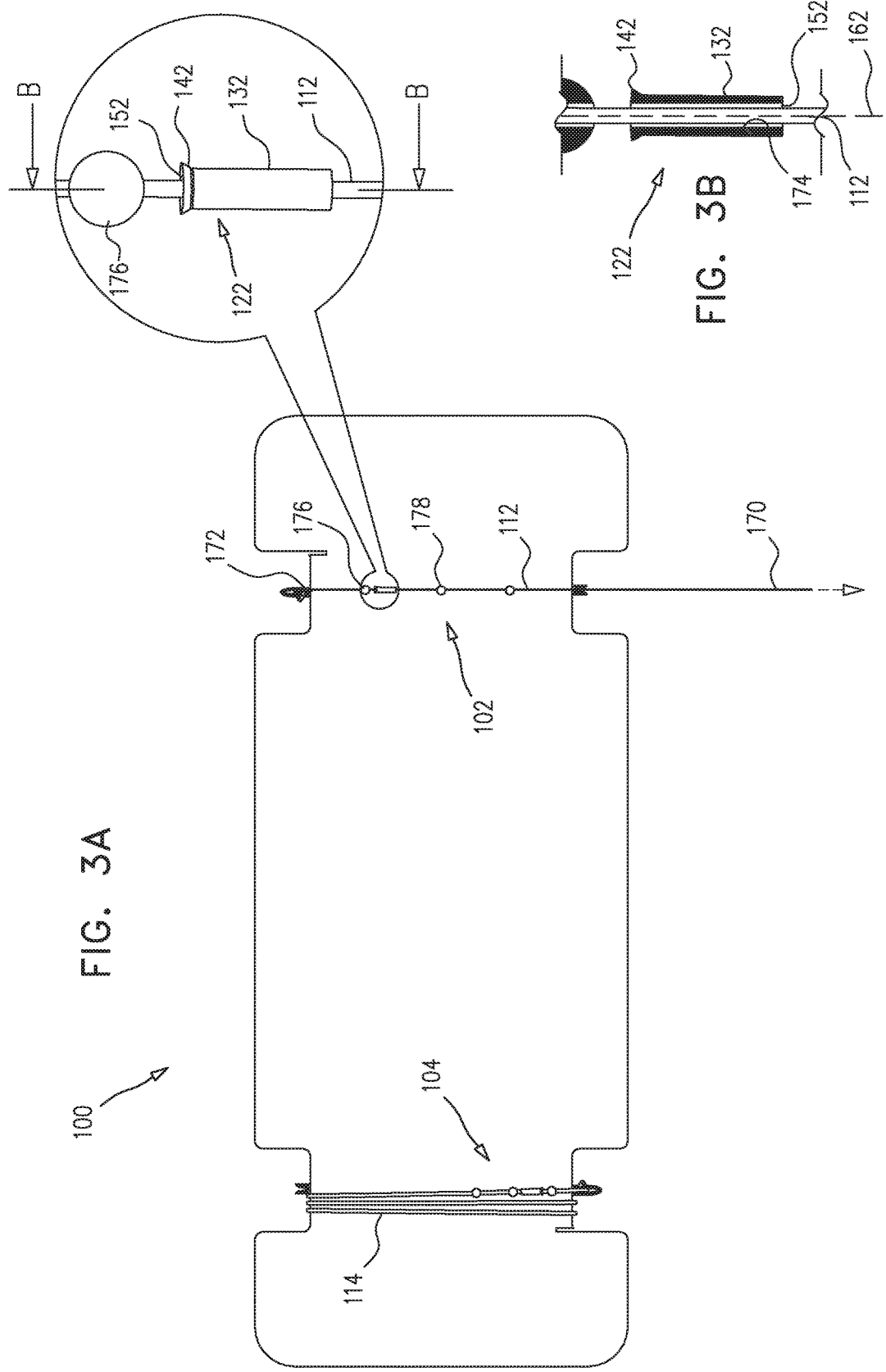

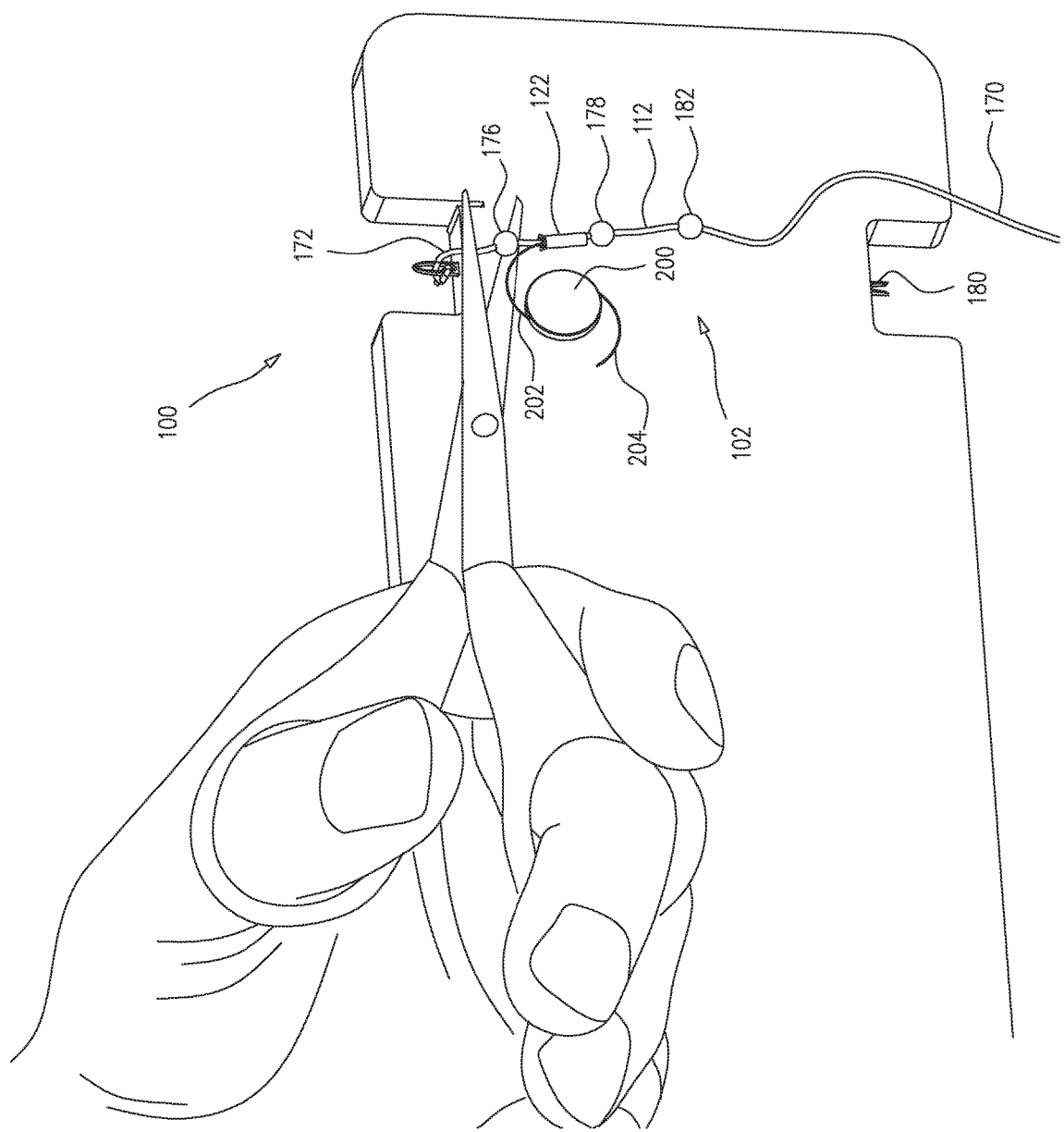

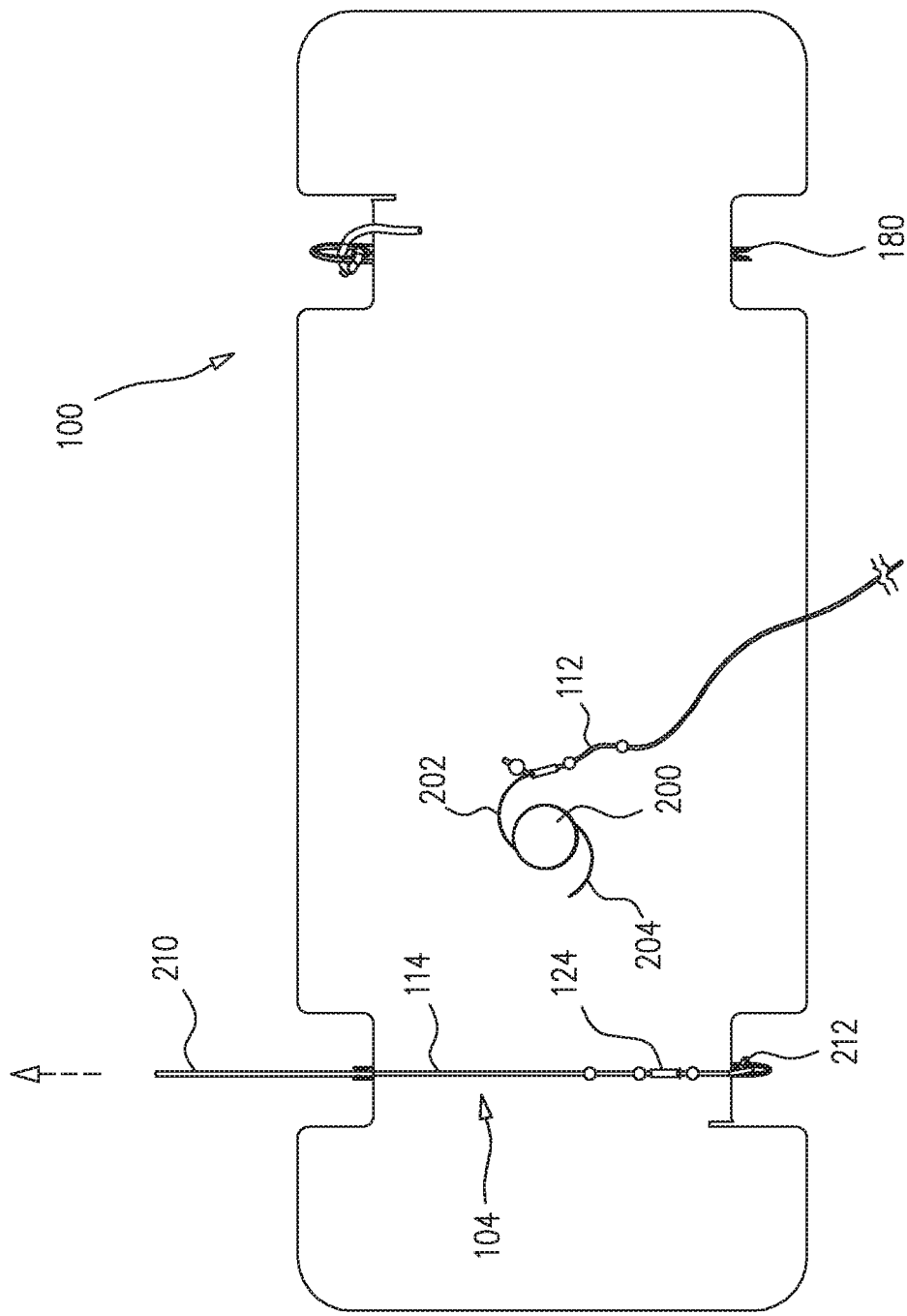

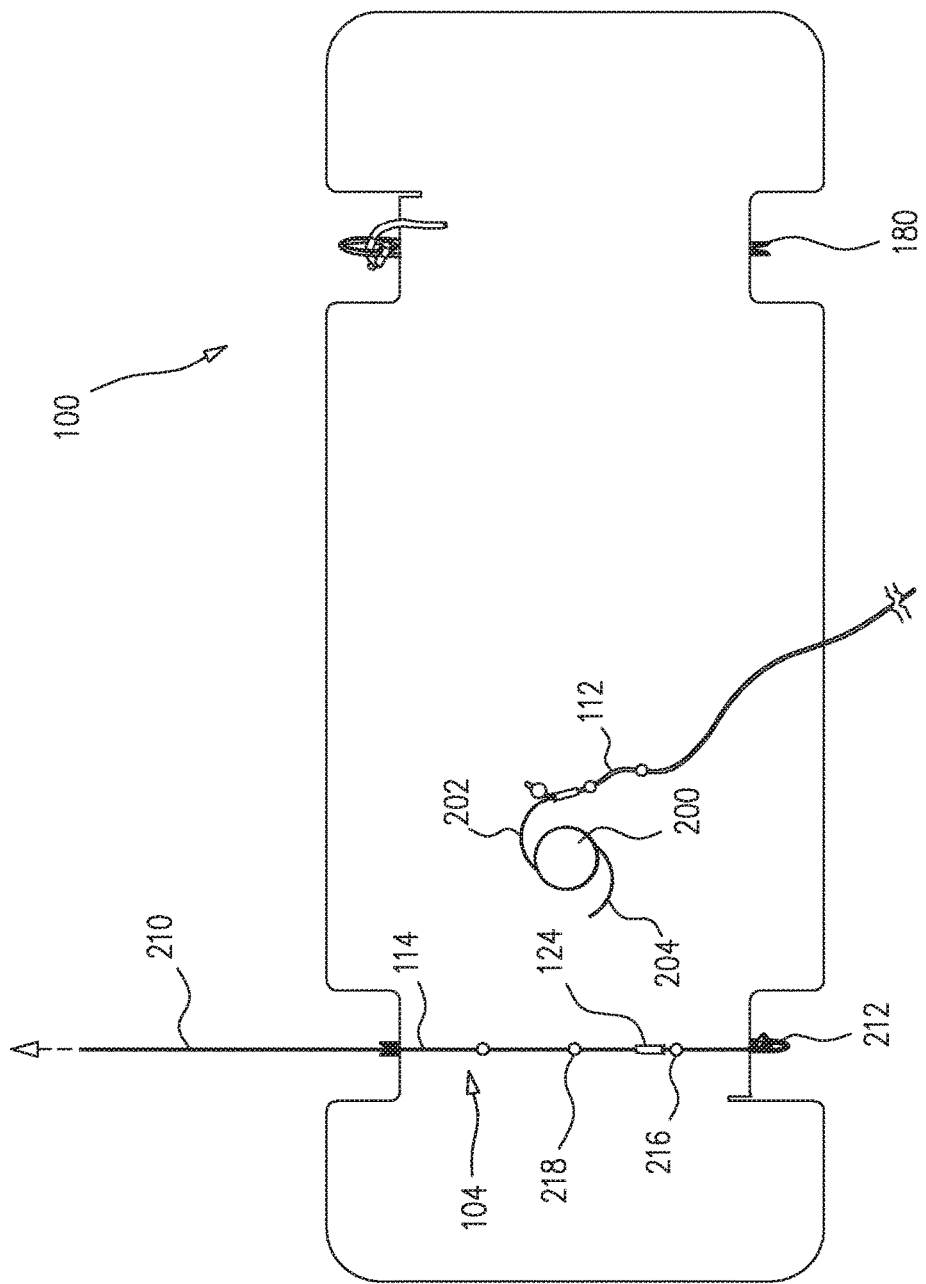

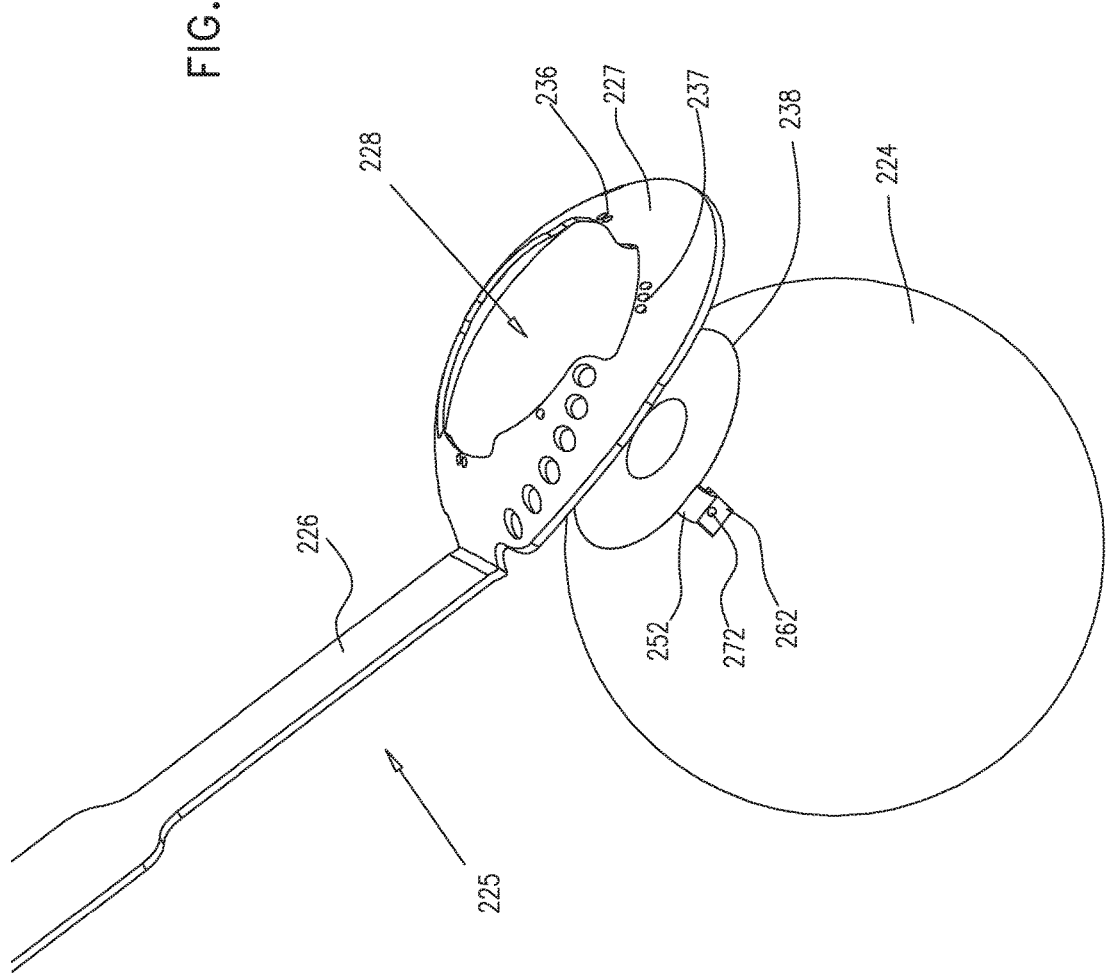

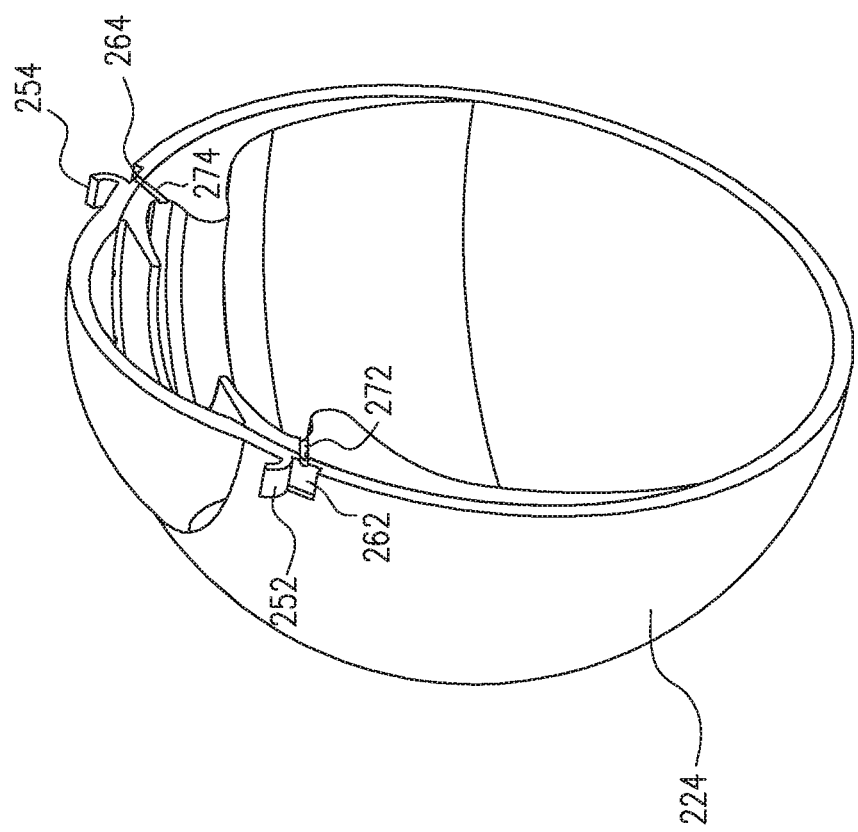

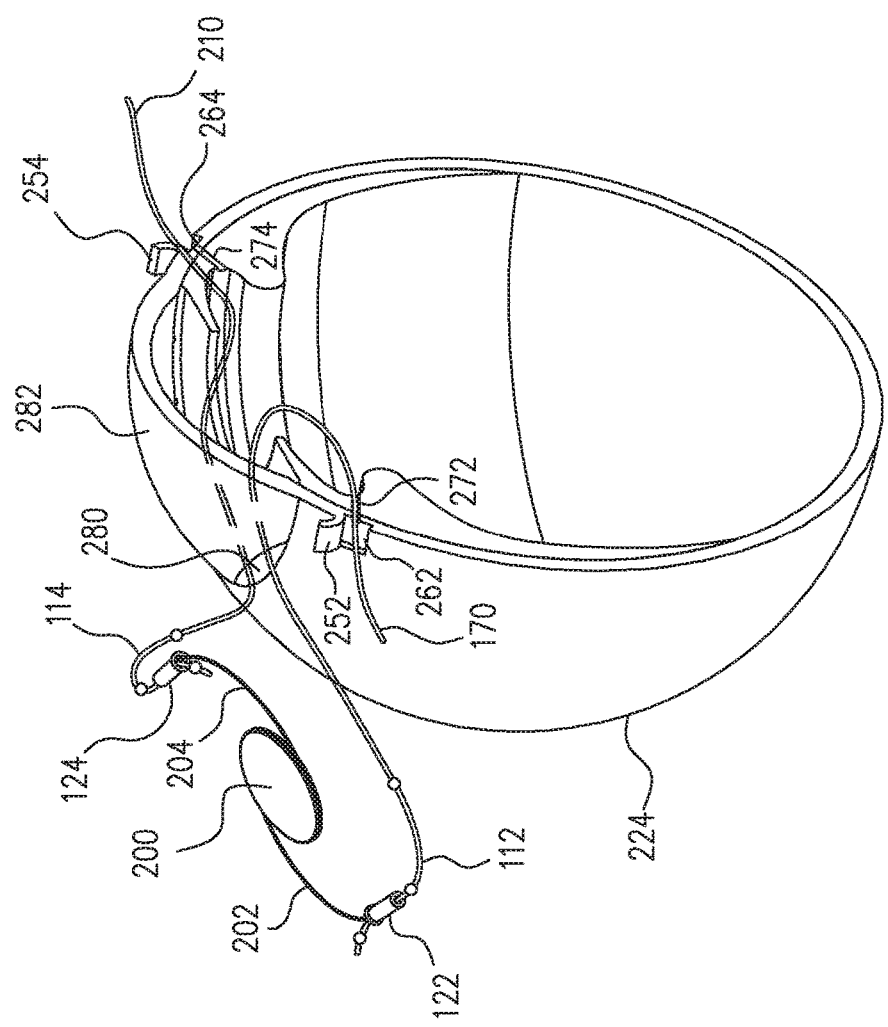

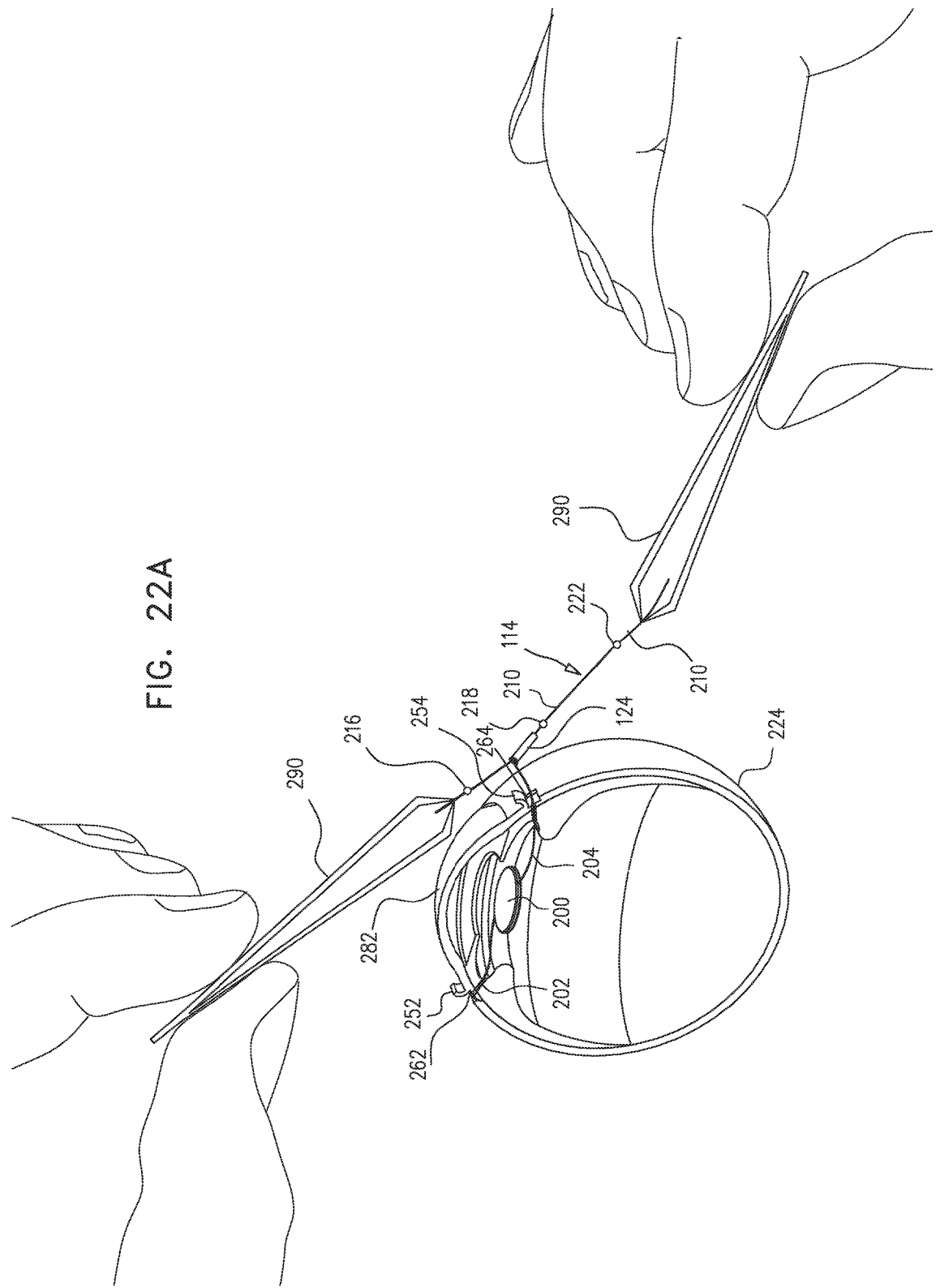

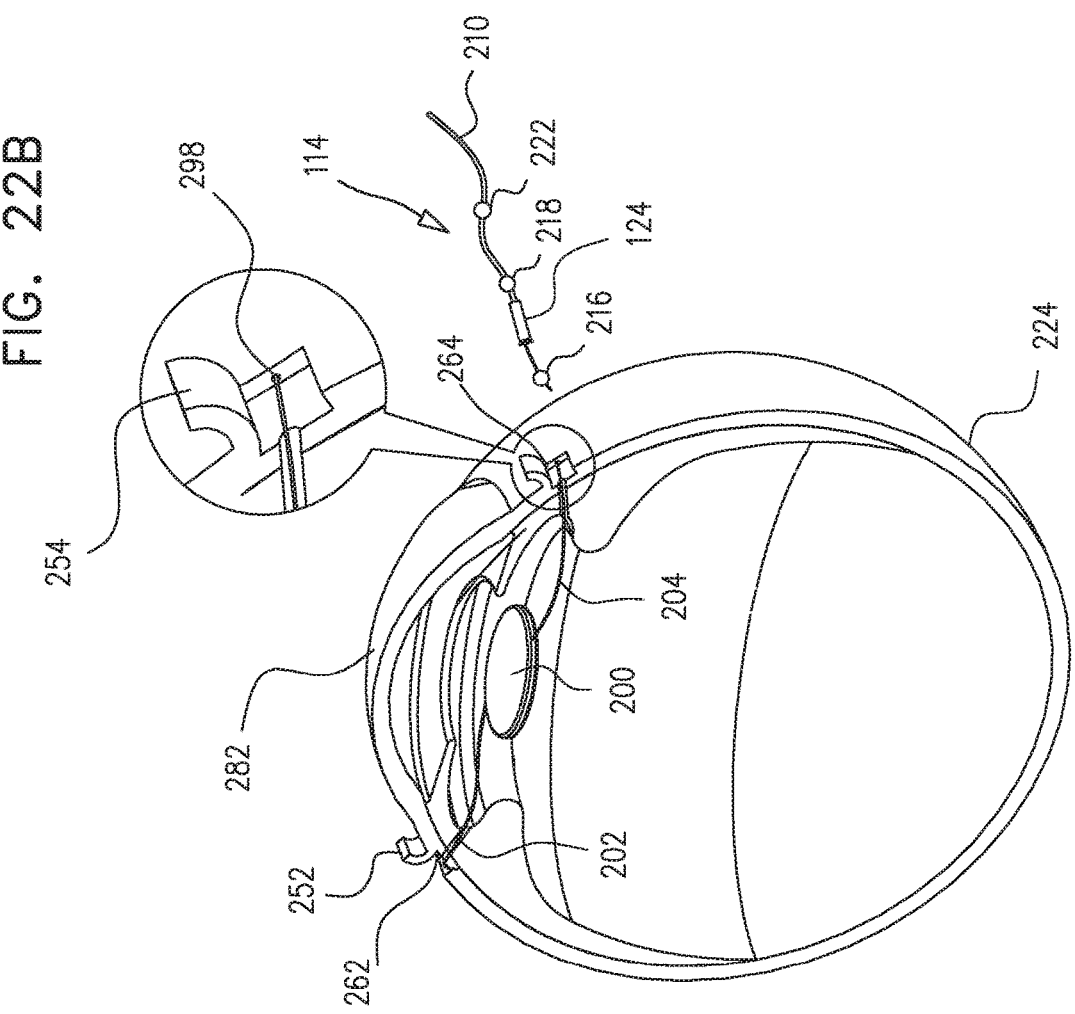

METHOD AND APPARATUS FOR PREPARATION AND INSERTION OF AN INTRAOCULAR LENS INTO THE EYE OF A PATIENT

REFERENCE TO RELATED APPLICATIONS

This application is a National Phase Application of PCT/IL2014/050955, filed Nov. 3, 2014, entitled "METHOD AND APPARATUS FOR PREPARATION AND INSERTION OF AN INTRAOCULAR LENS INTO THE EYE OF A PATIENT", which claims priority of U.S. Provisional Patent Application Ser. No. 62/031,255, entitled "METHOD AND APPARATUS FOR PREPARATION AND INSERTION OF AN INTRAOCULAR LENS INTO THE EYE OF A PATIENT", filed Jul. 31, 2014, and which is a continuation-in-part of U.S. patent application Ser. No. 14/070,958 filed Nov. 4, 2013 and entitled "METHOD AND APPARATUS FOR PREPARATION AND INSERTION OF AN INTRAOCULAR LENS INTO THE EYE OF A PATIENT", the disclosures of which are hereby incorporated by reference in their entirety.

This application is also a continuation-in-part of U.S. patent application Ser. No. 14/070,958 filed Nov. 4, 2013 and entitled "METHOD AND APPARATUS FOR PREPARATION AND INSERTION OF AN INTRAOCULAR LENS INTO THE EYE OF A PATIENT".

FIELD OF THE INVENTION

The present invention relates generally to intraocular lenses and methods and apparatus for insertion thereof into the eye of a patient.

BACKGROUND OF THE INVENTION

Pseudophakic patients for whom the original ocular capsular bag is not intact, for example as a result of cataract surgery or lens exchange, require novel methods and apparatus for the implantation and fixation of an intraocular lens within the patient's eye.

SUMMARY OF THE INVENTION

The present invention seeks to provide methods and apparatus for the implantation and fixation of an intraocular lens within the patient's eye.

There is thus provided in accordance with a preferred embodiment of the present invention an apparatus for preparation of an intraocular lens assembly prior to insertion thereof into the eye of a patient, the apparatus including a pair of elongate stretchable loop extension assemblies each including an elongate stretchable loop extension element, whose thickness varies as a function of an extent to which it is stretched, and a connector through which the elongate stretchable loop extension element is threaded.

Preferably, the connector includes a longitudinal cylindrical bore formed therewithin, the elongate stretchable loop extension element being threaded through the longitudinal cylindrical bore. Preferably, the connector includes a cylindrical portion and a funnel shaped portion.

Preferably, when the elongate stretchable loop extension element is in an unstretched configuration, a diameter of the elongate stretchable loop extension element is generally nearly equal to a diameter of the longitudinal cylindrical bore of the connector.

Preferably, when the elongate stretchable loop extension element is in a stretched configuration, a diameter of the elongate stretchable loop extension element is narrower than a diameter of the longitudinal cylindrical bore, thereby allowing for insertion of at least one additional element into the longitudinal cylindrical bore of the connector.

In accordance with one preferred embodiment of the present invention, the elongate stretchable loop extension element includes a pair of connector motion-limiting elements integrally formed thereon for limiting the motion of the corresponding connector therebetween when the elongate stretchable loop extension element is in the stretched configuration.

In accordance with an alternative embodiment of the present invention, the elongate stretchable loop extension element includes a pair of connector motion-limiting elements integrally formed thereon for retaining the connector therebetween in a partially pretensioned configuration, a section of the elongate stretchable loop extension element being stretchably threaded within the connector, thereby retaining the connector motion-limiting elements in tight engagement with the connector.

Preferably, after inserting at least one additional element into the longitudinal cylindrical bore of the connector when the elongate stretchable loop extension element is in the stretched configuration and then allowing the elongate stretchable loop extension element to return to an unstretched fastened configuration, the diameter of the elongate stretchable loop extension element returns to be generally nearly equal to a diameter of the longitudinal cylindrical bore of the connector, thereby tightly engaging the elongate stretchable loop extension element and the at least one additional element with an inner surface of the cylindrical bore of the longitudinal cylindrical bore of the connector, and thereby fastening the at least one additional element to the elongate stretchable loop extension element.

There is also provided in accordance with another preferred embodiment of the present invention a method for insertion of an intraocular lens into the eye of a patient, the method including removably attaching loop extensions to loops of an intraocular lens prior to insertion of the intraocular lens into the eye of a patient, initially inserting into the eye of the patient the loop extensions, pulling on the loop extensions through sclerectomies formed in the sclera of the eye of the patient, inserting the intraocular lens into the eye of the patient, positioning the intraocular lens in a desired position in the eye of the patient by pulling on the loop extensions through the sclerectomies, and fixing the loops to the sclera of the eye of the patient at the sclerectomies and detaching the loop extensions from the loops.

Preferably, each loop extension of the loop extensions includes an elongate stretchable loop extension element formed of stretchable elastomeric flexible material, a thickness of the elongate stretchable loop extension element varying as a function of an extent to which the elongate stretchable loop extension element is stretched.

Preferably, each loop extension of the loop extensions also includes a corresponding connector having a longitudinal cylindrical bore formed therewithin, the elongate stretchable loop extension element of the loop extension being threaded through the longitudinal cylindrical bore. Preferably, each of the connectors includes a cylindrical portion and a funnel shaped portion.

Preferably, removably attaching the loop extensions to the loops of the intraocular lens includes stretching and retaining the elongate stretchable loop extension element of each of the loop extensions from an unstretched unfastened configuration to a retained stretched configuration, while the elongate stretchable loop extension element is in the retained stretched configuration inserting an end of a corresponding one of the loops into the longitudinal cylindrical bore of the connector of the loop extension, and after inserting an end of a corresponding one of the loops into the longitudinal cylindrical bore of the connector of the loop extension, releasing the elongate stretchable loop extension element from the retained stretched configuration, thereby placing the elongate stretchable loop extension element in an unstretched fastened configuration.

Preferably, when the elongate stretchable loop extension element is in the unstretched unfastened configuration, a diameter of the elongate stretchable loop extension element is generally nearly equal to a diameter of the longitudinal cylindrical bore of the corresponding connector.

Preferably, when the elongate stretchable loop extension element is in the retained stretched configuration, a diameter of the elongate stretchable loop extension element is narrower than a diameter of the longitudinal cylindrical bore.

In accordance with one preferred embodiment of the present invention, the elongate stretchable loop extension element includes a pair of connector motion-limiting elements integrally formed thereon for limiting the motion of the corresponding connector therebetween when the elongate stretchable loop extension element is in the retained stretched configuration.

In accordance with an alternative embodiment of the present invention, each of the elongate stretchable loop extension elements includes a pair of connector motion-limiting elements integrally formed thereon for retaining the corresponding connector therebetween in a partially pretensioned configuration, a section of the elongate stretchable loop extension element being stretchably threaded within the corresponding connector, thereby retaining the connector motion-limiting elements in tight engagement with the corresponding connector.

Preferably, when the elongate stretchable loop extension element is in the unstretched fastened configuration, a diameter of the elongate stretchable loop extension element is generally nearly equal to a diameter of the longitudinal cylindrical bore of the corresponding connector, thereby tightly engaging the elongate stretchable loop extension element and the loop with an inner surface of the cylindrical bore of the longitudinal cylindrical bore of the corresponding connector, and thereby fastening the loop to the elongate stretchable loop extension element.

Preferably, pulling on the loop extensions through the sclerectomies formed in the sclera of the eye of the patient includes pulling the elongate stretchable loop extension elements of the loop extensions, the corresponding connectors of the loop extensions and the corresponding loops of the intraocular lens from within the sclera through the sclerectomies. Preferably, once pulled through the sclerectomies, each connector of the connectors is operative to serve as a motion-limiting element which prevents a corresponding one of the loops, the connector and a corresponding one of the elongate stretchable loop extension elements from being retracted into the sclera.

Preferably, detaching the loop extension from the loop includes stretching the elongate stretchable loop extension element of the loop extension from the unstretched fastened configuration to a stretched unfastened configuration, and releasing the loop from the connector.

Preferably, when elongate stretchable loop extension element is in the stretched unfastened configuration, a diameter of the elongate stretchable loop extension element is narrower than a diameter of the longitudinal cylindrical bore of the corresponding connector, thereby releasing the loop from an inner surface of the longitudinal cylindrical bore of the corresponding connector.

There is further provided in accordance with yet another preferred embodiment of the present invention, a method of preparation of an intraocular lens assembly prior to insertion thereof into the eye of a patient, the method including removably attaching loop extensions to loops of an intraocular lens. Preferably, removably attaching loop extensions to loops of an intraocular lens includes providing a pair of elongate stretchable loop extension assemblies each including an elongate stretchable loop extension element, whose thickness varies as a function of an extent to which it is stretched and a connector through which the elongate stretchable loop extension element is threaded, and removably inserting an end of each loop of the intraocular lens into a corresponding connector of one of the pair of elongate stretchable loop extension assemblies.

Preferably, the connector includes a longitudinal cylindrical bore formed therewithin, the elongate stretchable loop extension element being threaded through the longitudinal cylindrical bore. Preferably, the connector includes a cylindrical portion and a funnel shaped portion.

Preferably, removably inserting an end of each loop of the intraocular lens into a corresponding connector of one of the pair of elongate stretchable loop extension assemblies includes stretching and retaining the elongate stretchable loop extension element of each of the elongate stretchable loop extension assemblies from an unstretched unfastened configuration to a retained stretched configuration, while the elongate stretchable loop extension element is in the retained stretched configuration inserting an end of the loop into the longitudinal cylindrical bore of the corresponding connector of one of the pair of elongate stretchable loop extension assemblies, and after inserting an end of the loop into the longitudinal cylindrical bore of the corresponding connector of one of the pair of elongate stretchable loop extension assemblies, releasing the elongate stretchable loop extension element from the retained stretched configuration, thereby placing the elongate stretchable loop extension element in an unstretched fastened configuration.

Preferably, when the elongate stretchable loop extension element is in the unstretched unfastened configuration, a diameter of the elongate stretchable loop extension element is generally nearly equal to a diameter of the longitudinal cylindrical bore of the corresponding connector.

Preferably, when the elongate stretchable loop extension element is in the retained stretched configuration, a diameter of the elongate stretchable loop extension element is narrower than a diameter of the longitudinal cylindrical bore.

In accordance with one preferred embodiment of the present invention, the elongate stretchable loop extension element includes a pair of connector motion-limiting elements integrally formed thereon for limiting the motion of the corresponding connector therebetween when the elongate stretchable loop extension element is in the retained stretched configuration.

In accordance with an alternative embodiment of the present invention, the elongate stretchable loop extension element includes a pair of connector motion-limiting elements integrally formed thereon for retaining the connector therebetween in a partially pretensioned configuration, a section of the elongate stretchable loop extension element being stretchably threaded within the connector, thereby retaining the connector motion-limiting elements in tight engagement with the connector.

Preferably, when the elongate stretchable loop extension element is in the unstretched fastened configuration, a diameter of the elongate stretchable loop extension element is generally nearly equal to a diameter of the longitudinal cylindrical bore of the connector, thereby tightly engaging the elongate stretchable loop extension element and the loop with an inner surface of the cylindrical bore of the longitudinal cylindrical bore of the connector, and thereby fastening the loop to the elongate stretchable loop extension element.

There is yet further provided in accordance with still another preferred embodiment of the present invention an apparatus for guiding surgical formation of a pair of symmetrical sclerectomies in an eye of a patient, the apparatus including a multi-diameter generally circular cutout portion including at least a first portion having a first diameter and a second portion having a second diameter, the multi-diameter generally circular cutout portion being arranged for placement over the limbus of the eye and for centering the limbus within at least one of the at least first and second portions, thereby enabling estimating the diameter of the limbus to be approximately equal to the diameter of the at least one of the at least first and second portions centering the limbus therewithin, and at least first and second series of sclerectomy guiding apertures formed about the cutout portion, each first sclerectomy guiding aperture of the first series having a paired second sclerectomy guiding aperture in the second series formed 180° apart from the first sclerectomy guiding aperture relative to a center of the cutout portion, the at least first and second series of sclerectomy guiding apertures together including at least one pair of corresponding first and second sclerectomy guiding apertures having a diameter therebetween which is wider than the diameter of at least one of the first and second portions.

Preferably, the at least one pair of corresponding first and second sclerectomy guiding apertures is arranged for guiding surgical formation of a pair of symmetrical sclerectomies in the sclera of an eye of a patient. Preferably, each first sclerectomy guiding aperture of the first series and paired second sclerectomy guiding aperture of the second series are formed at equal distances from the cutout portion. Preferably, the first sclerectomy guiding apertures of the first series are formed at varying distances from the cutout portion.

Preferably, the second diameter is wider than the first diameter. Preferably, the apparatus also includes a handle portion and a spherical cap portion, the spherical cap portion including the multi-diameter generally circular cutout portion formed therewithin. Preferably, the apparatus also includes at least a pair of single positioning indicators formed on an edge of the first portion and a pair of double positioning indicators formed on an edge of the second portion, the positioning indicators indicating, to an operator of the apparatus, the position of the first and second portions.

Preferably, the multi-diameter generally circular cutout portion also includes a third portion having a third diameter, the at least first and second series of sclerectomy guiding apertures together including at least one pair of corresponding first and second sclerectomy guiding apertures having a diameter therebetween which is wider than the diameter of the third portion. Preferably, the third diameter is wider than the second diameter. Preferably, the apparatus also includes a pair of triple positioning indicators formed on an edge of the third portion.

There is also provided in accordance with another preferred embodiment of the present invention a method for guiding surgical formation of a pair of symmetrical sclerectomies in an eye of a patient, the method including placing a multi-diameter generally circular cutout over the limbus of the eye and centering the limbus therewithin, the cutout including at least a first portion having a first diameter and a second portion having a second diameter, estimating the diameter of the limbus to be approximately equal to the diameter of at least one of at least first and second portions of the cutout, and selecting at least one pair of first and second sclerectomy guiding apertures for guiding surgical formation of a pair of symmetrical sclerectomies in the sclera of an eye of a patient, the at least one pair of first and second sclerectomy guiding apertures being formed about the cutout 180° thereapart relative to a center of the cutout and having a diameter therebetween which is wider than the diameter of at least one of the first and second portions.

Preferably, each of the at least one pair of first and second sclerectomy guiding apertures are formed at equal distances from the cutout. Preferably, the second diameter is wider than the first diameter. Preferably, the method also includes employing at least a pair of single positioning indicators formed on an edge of the first portion and a pair of double positioning indicators formed on an edge of the second portion, the positioning indicators being operative to indicate the position of the first and second portions.

There is also provided in accordance with another preferred embodiment of the present invention and apparatus for guiding surgical formation of a pair of symmetrical sclerectomies in an eye of a patient, the apparatus comprising a generally circular cutout portion, the generally circular cutout portion being arranged for placement over the limbus of the eye and for centering the limbus therewithin, thereby enabling estimating the diameter of the limbus to be approximately equal to the diameter of the generally circular cutout portion centering the limbus therewithin, and at least first and second series of sclerectomy guiding apertures formed about the cutout portion, each first sclerectomy guiding aperture of the first series having a paired second sclerectomy guiding aperture in the second series formed 180° apart from the first sclerectomy guiding aperture relative to a center of the cutout portion, the at least first and second series of sclerectomy guiding apertures together comprising at least one pair of corresponding first and second sclerectomy guiding apertures having a distance therebetween which is wider than the diameter of the generally circular cutout portion.

Preferably, the at least one pair of corresponding first and second sclerectomy guiding apertures is arranged for guiding surgical formation of a pair of symmetrical sclerectomies in the sclera of an eye of a patient. Preferably, each first sclerectomy guiding aperture of the first series and the paired second sclerectomy guiding aperture of the second series are formed at equal distances from the cutout portion.

Preferably, the first sclerectomy guiding apertures of the first series are formed at varying distances from the cutout portion. Preferably, the apparatus also includes a handle portion and a spherical cap portion, the spherical cap portion comprising the generally circular cutout portion formed therewithin.

There is further provided in accordance with yet another preferred embodiment of the present invention a method for guiding surgical formation of a pair of symmetrical sclerectomies in an eye of a patient, the method comprising placing a generally circular cutout over the limbus of the eye and centering the limbus therewithin, estimating the diameter of the limbus to be approximately equal to the diameter of the generally circular cutout, and selecting at least one pair of first and second sclerectomy guiding apertures for guiding surgical formation of a pair of symmetrical sclerectomies in the sclera of an eye of a patient, the at least one pair of first and second sclerectomy guiding apertures being formed about the cutout 180° thereapart relative to a center of the cutout and having a diameter therebetween which is wider than the diameter of the generally circular cutout. Preferably, each of the at least one pair of first and second sclerectomy guiding apertures are formed at equal distances from the cutout.

There is further provided in accordance with yet another preferred embodiment of the present invention a method for guiding surgical formation of a pair of symmetrical sclerectomies in an eye of a patient, the method including projecting an image of a multi-diameter generally circular cutout over the limbus of the eye and centering the limbus therewithin, the cutout including at least a first portion having a first diameter and a second portion having a second diameter, estimating the diameter of the limbus to be approximately equal to the diameter of at least one of at least first and second portions of the cutout, and selecting at least one pair of first and second sclerectomy guiding apertures for guiding surgical formation of a pair of symmetrical sclerectomies in the sclera of an eye of a patient, the at least one pair of first and second sclerectomy guiding apertures being positioned about the cutout 180° thereapart relative to a center of the cutout and having a diameter therebetween which is wider than the diameter of at least one of the first and second portions.

Preferably, each of the at least one pair of first and second sclerectomy guiding apertures are positioned at equal distances from the cutout. Preferably, the second diameter is wider than the first diameter. Preferably, the method also includes employing at least a pair of single positioning indicators positioned on an edge of the first portion and a pair of double positioning indicators positioned on an edge of the second portion, the positioning indicators being operative to indicate the position of the first and second portions.

There is further provided in accordance with yet another preferred embodiment of the present invention a method for guiding surgical formation of a pair of symmetrical sclerectomies in an eye of a patient, the method comprising projecting an image of a generally circular cutout over the limbus of the eye and centering the limbus therewithin, estimating the diameter of the limbus to be approximately equal to the diameter of the generally circular cutout, and selecting at least one pair of first and second sclerectomy guiding apertures for guiding surgical formation of a pair of symmetrical sclerectomies in the sclera of an eye of a patient, the at least one pair of first and second sclerectomy guiding apertures being positioned about the cutout 180° thereapart relative to a center of the generally circular cutout and having a diameter therebetween which is wider than the diameter of the generally circular cutout. Preferably, each of the at least one pair of first and second sclerectomy guiding apertures are positioned at equal distances from the cutout.

BRIEF DESCRIPTION OF THE DRAWINGS

The present invention will be understood and appreciated more fully from the following detailed description taken in conjunction with the drawings in which:

FIG. 1A is a simplified pictorial illustration of an apparatus for preparation of an intraocular lens assembly, constructed in accordance with a preferred embodiment of the present invention;

FIG. 1B is a simplified sectional view of a connector which is part of the apparatus of FIG. 1A, the sectional view being taken along lines B-B of FIG. 1A;

FIG. 1C is a simplified pictorial illustration of an apparatus for preparation of an intraocular lens assembly, constructed in accordance with an alternative embodiment of the present invention;

FIG. 1D is a simplified sectional view of a connector which is part of the apparatus of FIG. 1C, the sectional view being taken along lines D-D of FIG. 1C;

FIG. 2A is a simplified pictorial illustration of a first step in the operation of the apparatus of FIGS. 1A & 1B;

FIG. 2B is a simplified sectional view of a connector which is part of the apparatus of FIGS. 1A & 1B, the sectional view being taken along lines B-B of FIG. 2A;

FIG. 3A is a simplified pictorial illustration of a second step in the operation of the apparatus of FIGS. 1A & 1B;

FIG. 3B is a simplified sectional view of a connector which is part of the apparatus of FIG. 1, the sectional view being taken along lines B-B of FIG. 3A;

FIG. 8 is a simplified pictorial illustration of a seventh step in the operation of the apparatus of FIGS. 1A & 1B;

FIG. 9 is a simplified pictorial illustration of an eighth step in the operation of the apparatus of FIGS. 1A & 1B;

FIG. 10 is a simplified pictorial illustration of a ninth step in the operation of the apparatus of FIGS. 1A & 1B;

FIGS. 17B, 17C and 17D are simplified pictorial illustrations of an eye of a patient prepared for insertion of an intraocular lens which is part of the intraocular lens assembly of FIG. 16, via a pair of sclerectomies formed in the eye;

FIG. 18 is a simplified pictorial illustration of a first step in the implanting of an intraocular lens which is part of the intraocular lens assembly of FIG. 16 into an eye of a patient;

FIGS. 22A and 22B are simplified pictorial illustrations of a fifth step in the implanting of an intraocular lens which is part of the intraocular lens assembly of FIG. 16 into an eye of a patient;

DETAILED DESCRIPTION OF PREFERRED EMBODIMENTS

Figure 4:
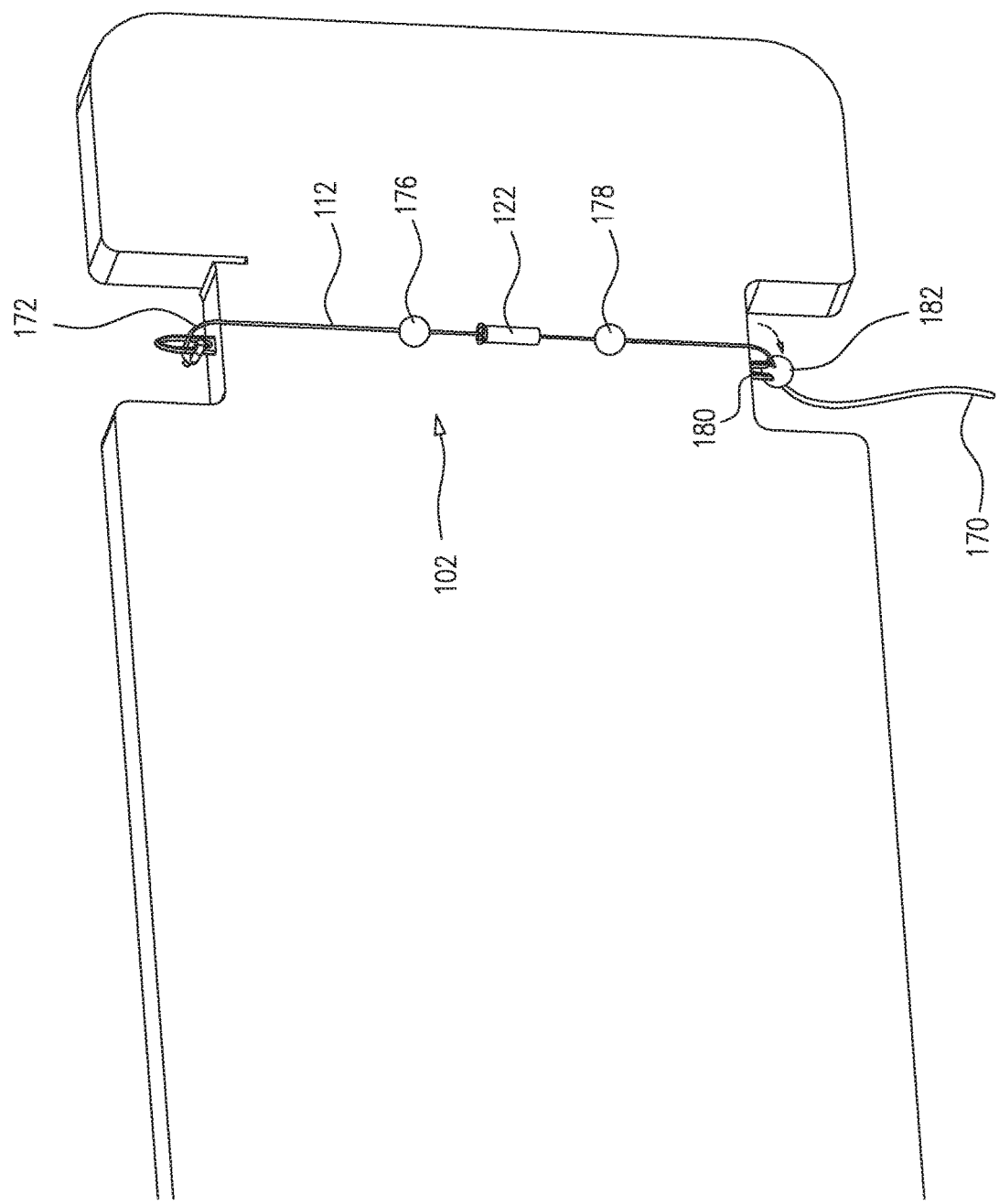
FIG. 4 is a simplified pictorial illustration of a third step in the operation of the apparatus of FIGS. 1A & 1B.
Figure 5:
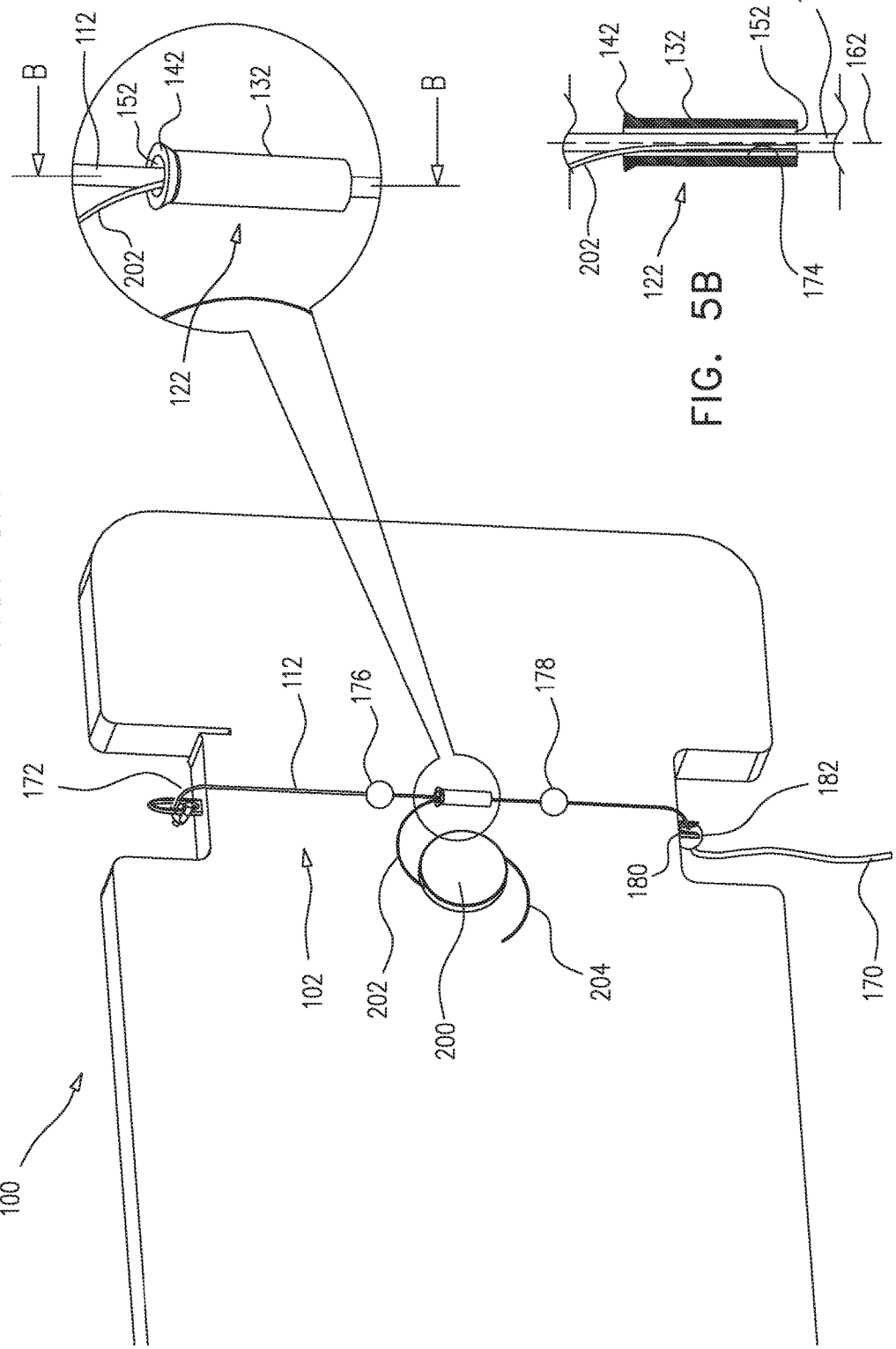
FIG. 5A is a simplified pictorial illustration of a fourth step in the operation of the apparatus of FIGS. 1A & 1B.
FIG. 5B is a simplified sectional view of a connector which is part of the apparatus of FIG. 1, the sectional view being taken along lines B-B of FIG. 5A.

Reference is now made to FIG. 1A, which is a simplified pictorial illustration of an apparatus for preparation of an intraocular lens assembly, constructed in accordance with a preferred embodiment of the present invention, and to FIG. 1B, which is a simplified sectional view of a connector which is part of the apparatus of FIG. 1A, the sectional view being taken along lines B-B of FIG. 1A. The novel apparatus and surgical procedure associated therewith and described hereinbelow, in which an intraocular lens is placed within the sulcus of a patient's eye and thereafter fixed to the sclera of the eye, is particularly suitable for pseudophakic patients for whom the capsular bag is not intact, for example as a result of cataract surgery or lens exchange. It is appreciated that this novel apparatus and surgical procedure is also suitable for any surgical procedure which involves implantation of intraocular devices such as, for example, an artificial iris or an intraocular telescopic lens.

As shown in FIGS. 1A & 1B, the apparatus 100 includes a pair of elongate stretchable loop extension assemblies 102 and 104, which include corresponding elongate stretchable loop extension elements 112 and 114, preferably formed of elastomeric flexible material, and whose thickness varies as a function of an extent to which it is stretched. Elongate stretchable loop extension assemblies 102 and 104 also include corresponding connectors 122 and 124 through which corresponding elongate stretchable loop extension elements 112 and 114 are threaded. Connectors 122 and 124 preferably include corresponding cylindrical portions 132 and 134 and corresponding funnel shaped portions 142 and 144. Cylindrical bores 152 and 154 are preferably formed within respective connectors 122 and 124 along corresponding axes 162 and 164.

Reference is now made to FIG. 1C, which is a simplified pictorial illustration of apparatus 100 constructed in accordance with an alternative embodiment of the present invention, and to FIG. 1D, which is a simplified sectional view of connector 122 of apparatus 100 of FIG. 1C, the sectional view being taken along lines D-D of FIG. 1C.

As shown in the alternative embodiment of FIGS. 1C & 1D, connector motion-limiting elements 166 and 168 are formed on elongate stretchable loop extension element 112 for retaining connector 122 therebetween in a partially pretensioned configuration, wherein a section of elongate stretchable loop extension element 112 disposed within connector 122 is stretched, thereby retaining elements 166 and 168 in tight engagement with connector 122.

Reference is now made to FIGS. 2A, 3A, 4, 5A, 6, 7A, 8, 9, 10, 11, 12, 13, 14 and 15, which are simplified pictorial illustrations of steps in the operation of apparatus 100, and to FIGS. 2B, 3B, 5B and 7B which are simplified sectional views of connector 122, the sectional view being taken along lines B-B of respective FIGS. 2A, 3A, 5A and 7A. It is appreciated that although FIGS. 2A-15 illustrate steps in the operation of apparatus 100 as illustrated in the embodiment of FIGS. 1A & 1B, the same steps may be executed in the operation of apparatus 100 as illustrated in the alternative embodiment of FIGS. 1C & 1D.

As shown in FIG. 2A, in the first step in the operation of apparatus 100, elongate stretchable loop extension element 112 of elongate stretchable loop extension assembly 102 is unwound from the apparatus 100 to an unstretched configuration. As clearly seen in the unwound configuration of FIG. 2A, elongate stretchable loop extension element 112 has a loose end 170 and a retained end 172 retained on apparatus 100.

It is a particular feature of this preferred embodiment of the present invention that in the unstretched configuration of FIGS. 2A & 2B, the diameter of elongate stretchable loop extension element 112 is generally nearly equal to the diameter of cylindrical bore 152.

As further shown in FIG. 3A, in the second step in the operation of apparatus 100, elongate stretchable loop extension element 112 of elongate stretchable loop extension assembly 102 is stretched from the apparatus 100 to a stretched configuration by a user pulling on loose end 170.

It is a another particular feature of this preferred embodiment of the present invention that in the stretched configuration of FIGS. 3A & 3B, the diameter of elongate stretchable loop extension element 112 is narrower than the diameter of cylindrical bore 152, thereby allowing for insertion of additional elements into connector 122. A pair of connector motion-limiting elements 176 and 178 are preferably formed on elongate stretchable loop extension element 112 for limiting the motion of connector 122 therebetween on elongate stretchable loop extension element 112.

Turning now to FIG. 4, it is shown that in the third step in the operation of apparatus 100, loose end 170 of elongate stretchable loop extension element 112 is further stretched through a fork-shaped retaining element 180 formed on apparatus 100 and is retained therein by an extension element retaining element 182 formed on elongate stretchable loop extension element 112.

As further shown in FIGS. 5A & 5B, in a fourth step of the operation of apparatus 100, an intraocular lens 200 having loops 202 and 204 is brought into close proximity to elongate stretchable loop extension element 112, and loop 202 is inserted into bore 152 of connector 122 via funnel shaped portion 142. It is appreciated that loops 202 and 204 may be oriented either clockwise or counterclockwise with respect to intraocular lens 200. As described hereinabove, in the stretched configuration, the diameter of elongate stretchable loop extension element 112 is narrower than the diameter of cylindrical bore 152, thereby allowing insertion of elements other than elongate stretchable loop extension element 112 into connector 122.

Figure 6:
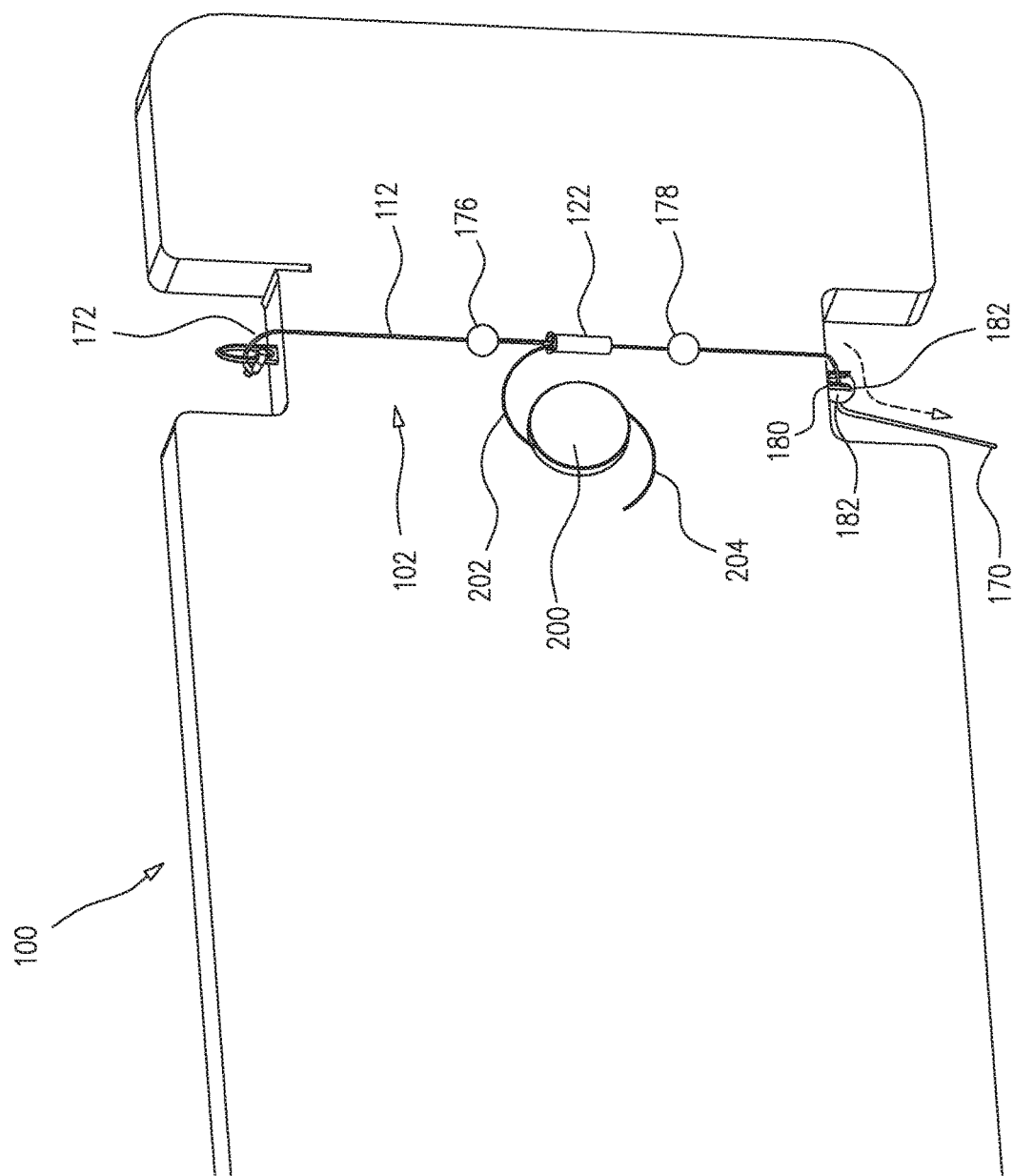
FIG. 6 is a simplified pictorial illustration of a fifth step in the operation of the apparatus of FIGS. 1A & 1B.
Figure 7A:
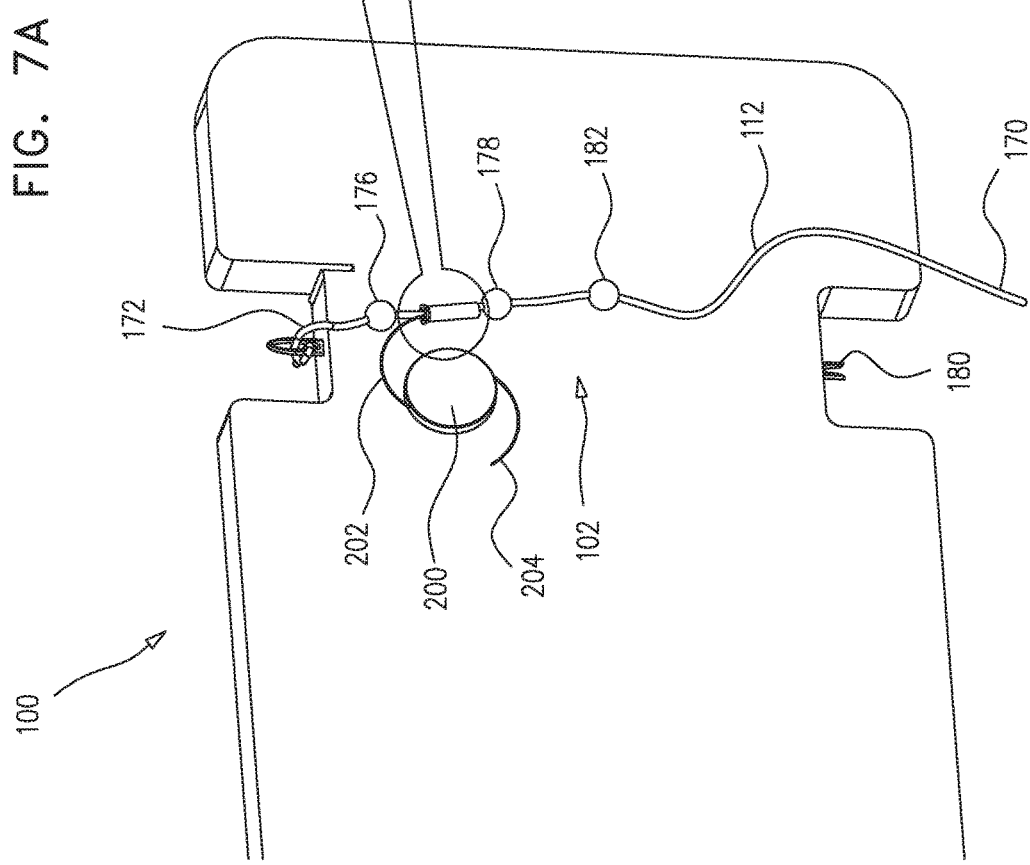
FIG. 7A is a simplified pictorial illustration of a sixth step in the operation of the apparatus of FIGS. 1A & 1B.
Figure 7B:
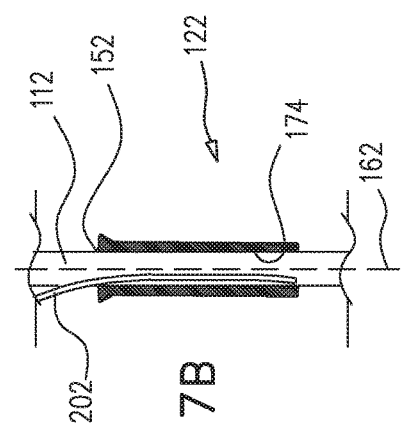
FIG. 7B is a simplified sectional view of a connector which is part of the apparatus of FIG. 1, the sectional view being taken along lines B-B of FIG. 7A.

Thereafter, in a fifth step of the operation of apparatus 100 shown in FIG. 6, extension element retaining element 182 is released from fork-shaped retaining element 180 of apparatus 100, thereby releasing elongate stretchable loop extension element 112. As further shown in FIGS. 7A & 7B, in a sixth step of the operation of apparatus 100, release of elongate stretchable loop extension element 112 from fork-shaped retaining element 180 allows elongate stretchable loop extension element 112 to return to the unstretched configuration wherein the diameter of elongate stretchable loop extension element 112 is generally nearly equal to the diameter of cylindrical bore 152, thereby tightly engaging elongate stretchable loop extension element 112 and loop 202 with inner surface 174 of cylindrical bore 152, and thereby fastening loop 202 to elongate stretchable loop extension element 112.

Thereafter, as shown in FIG. 8, in a seventh step of the operation of apparatus 100, the user of apparatus 100 preferably employs a pair of surgical scissors to sever elongate stretchable loop extension element 112 between retained end 172 and connector motion-limiting element 176, thereby disconnecting elongate stretchable loop extension element 112 along with loop 202 connected thereto, from apparatus 100.

Turning now to FIG. 9, it is shown that in an eighth step of the operation of apparatus 100, elongate stretchable loop extension element 114 of elongate stretchable loop extension assembly 104 is unwound from the apparatus 100 to an unstretched configuration. As clearly seen in FIG. 9, in the unwound configuration, elongate stretchable loop extension element 114 has a loose end 210 and a retained end 212 retained on apparatus 100.

As described hereinabove with reference to FIGS. 2A and 2B, it is a particular feature of this preferred embodiment of the present invention that in the unstretched configuration of FIG. 9, the diameter of elongate stretchable loop extension element 114 is generally nearly equal to the diameter of cylindrical bore 154 of connector 124.

Thereafter, in a ninth step of the operation of apparatus 100 shown in FIG. 10, elongate stretchable loop extension element 114 of elongate stretchable loop extension assembly 104 is stretched from the apparatus 100 to a stretched configuration by a user pulling on loose end 210.

As described hereinabove with reference to FIGS. 3A and 3B, it is a particular feature of this preferred embodiment of the present invention that in the stretched configuration of FIG. 10, the diameter of elongate stretchable loop extension element 114 is narrower than the diameter of cylindrical bore 154 thereby allowing for insertion of additional elements into connector 124. A pair of connector motion-limiting elements 216 and 218 are preferably formed on elongate stretchable loop extension element 114 for limiting the motion of connector 124 therebetween on elongate stretchable loop extension element 114.

Figure 11:
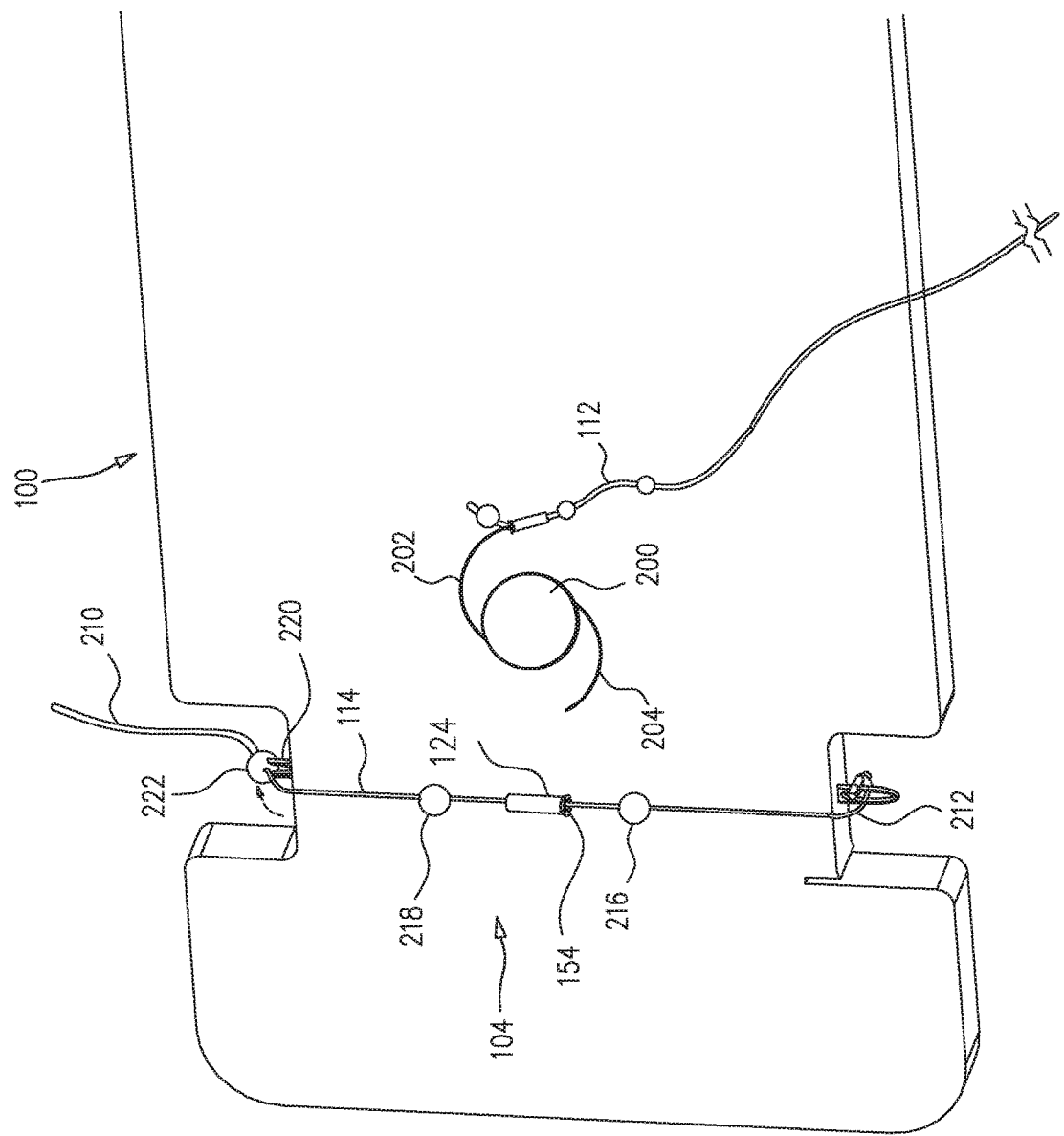
FIG. 11 is a simplified pictorial illustration of a tenth step in the operation of the apparatus of FIGS. 1A & 1B.

Turning now to FIG. 11, it is shown that in the tenth step in the operation of apparatus 100, loose end 210 of elongate stretchable loop extension element 114 is further stretched through a fork-shaped retaining element 220 formed on apparatus 100 and is retained therein by an extension element retaining element 222 formed on elongate stretchable loop extension element 114.

Figure 12:
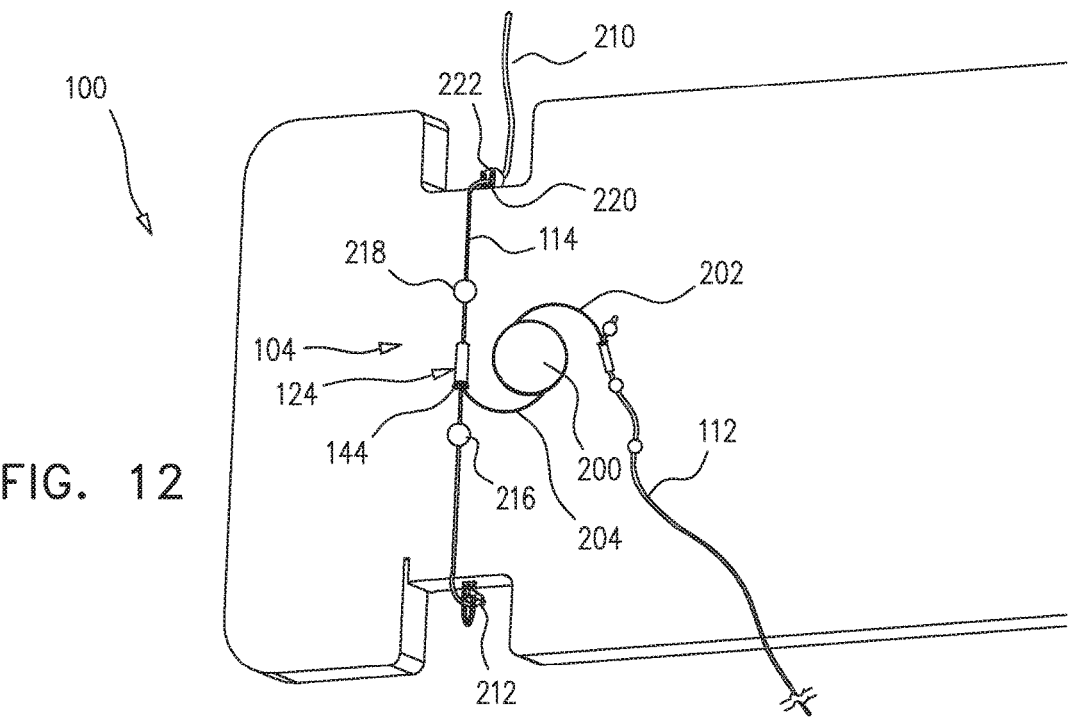
FIG. 12 is a simplified pictorial illustration of an eleventh step in the operation of the apparatus of FIGS. 1A & 1B.

Thereafter, in an eleventh step of the operation of apparatus 100 shown in FIG. 12, intraocular lens 200 is brought into close proximity to elongate stretchable loop extension element 114, and loop 204 is inserted into bore 154 of connector 124 via funnel shaped portion 144. As described hereinabove, in the stretched configuration, the diameter of elongate stretchable loop extension element 114 is narrower than the diameter of cylindrical bore 154, thereby allowing insertion of elements other than elongate stretchable loop extension element 114 into connector 124.

Figure 13:
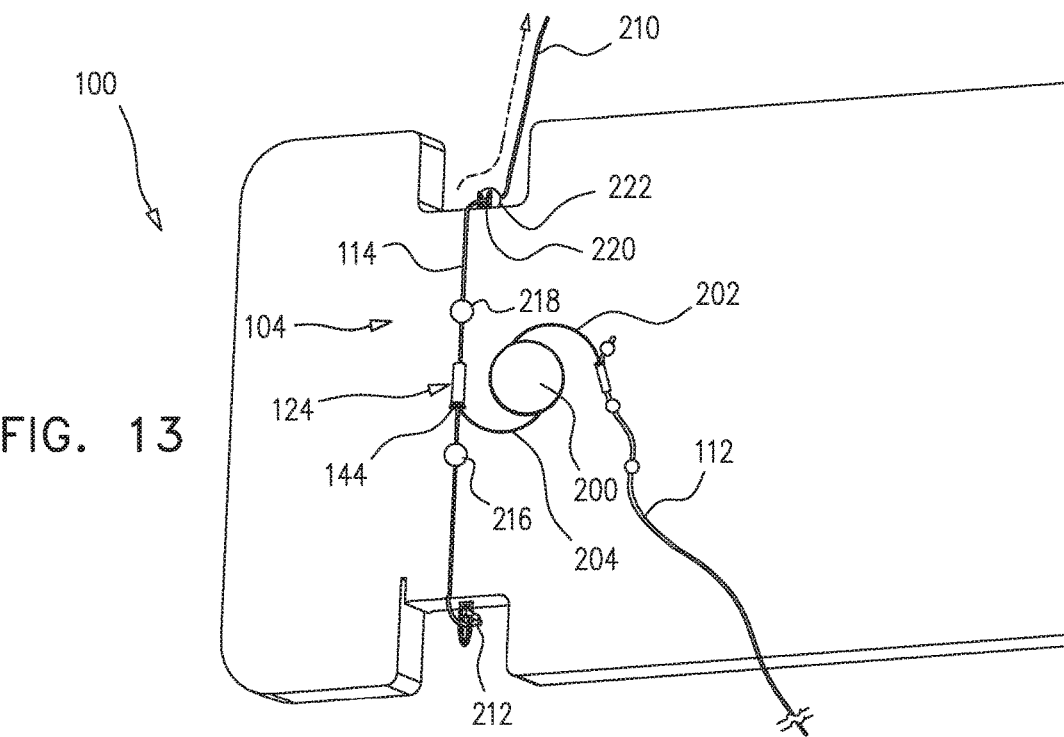
FIG. 13 is a simplified pictorial illustration of a twelfth step in the operation of the apparatus of FIGS. 1A & 1B.
Figure 14:
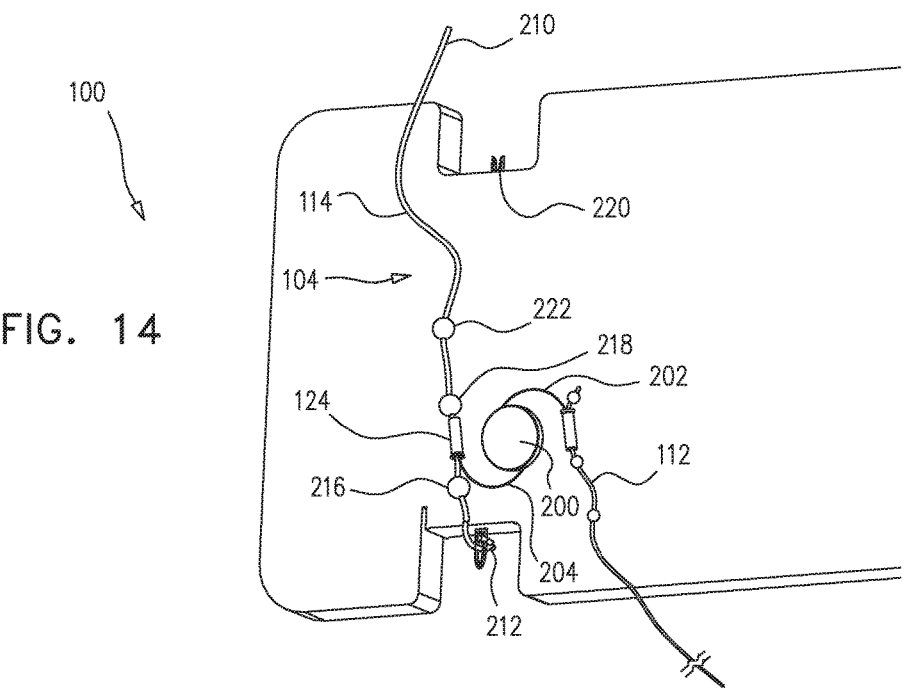
FIG. 14 is a simplified pictorial illustration of a thirteenth step in the operation of the apparatus of FIGS. 1A & 1B.

Turning now to FIG. 13, it is shown that in a twelfth step of the operation of apparatus 100, extension element retaining element 222 is released from fork-shaped retaining element 220 of apparatus 100, thereby releasing elongate stretchable loop extension element 114. As further shown in FIG. 14, in a thirteenth step of the operation of apparatus 100, release of elongate stretchable loop extension element 114 from fork-shaped retaining element 220 allows elongate stretchable loop extension element 114 to return to the unstretched configuration wherein the diameter of elongate stretchable loop extension element 114 is generally nearly equal to the diameter of cylindrical bore 154, thereby tightly engaging elongate stretchable loop extension element 114 and loop 204 with inner surface 214 of cylindrical bore 154, and thereby fastening loop 204 to elongate stretchable loop extension element 114.

Figure 15:
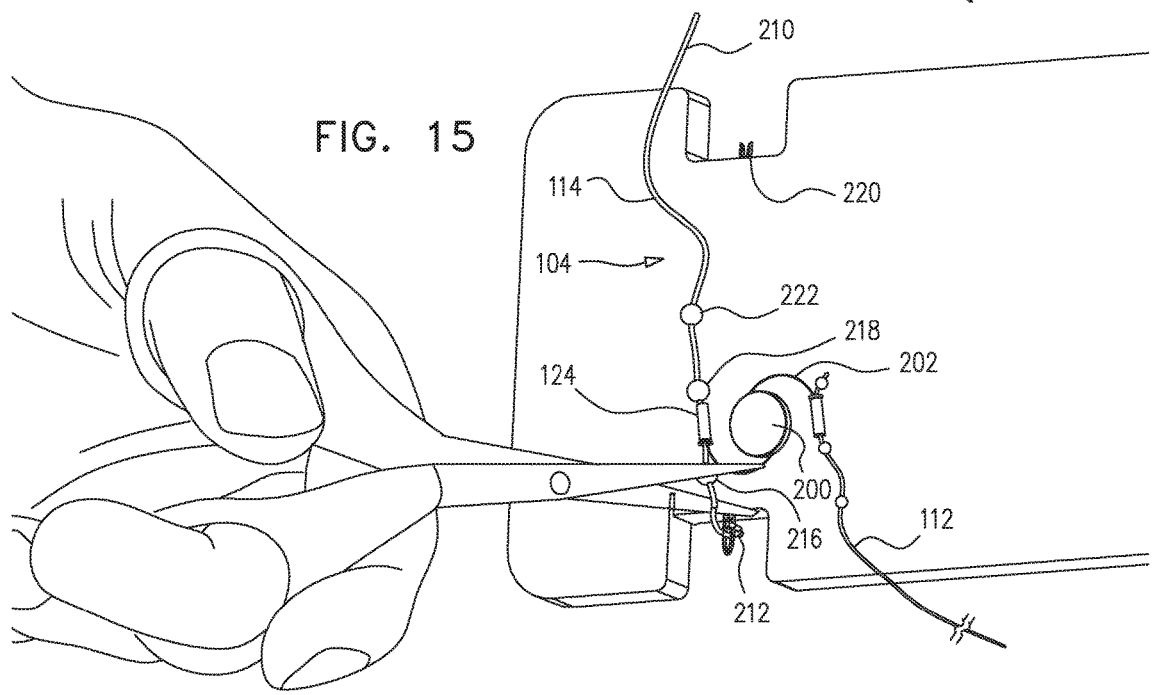
FIG. 15 is a simplified pictorial illustration of a fourteenth step in the operation of the apparatus of FIGS. 1A & 1B.

Thereafter, in a fourteenth step of the operation of apparatus 100 shown in FIG. 15, the user of apparatus 100 preferably employs a pair of surgical scissors to sever elongate stretchable loop extension element 114 between retained end 212 and connector motion-limiting element 216, thereby disconnecting elongate stretchable loop extension element 114 along with loop 204 connected thereto, from apparatus 100.

Figure 16:
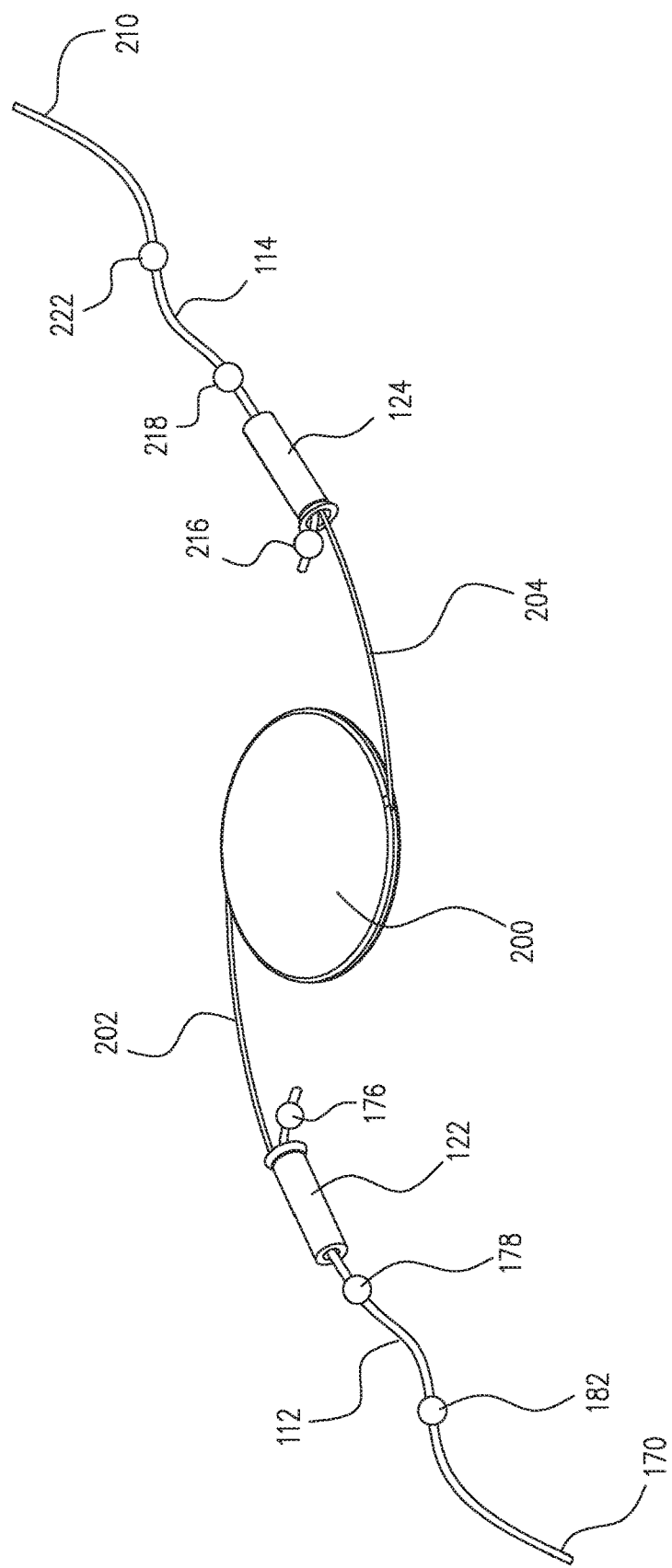
FIG. 16 is a simplified pictorial illustration of an example of an intraocular lens assembly prepared by employing the apparatus of FIG. 1.

Reference is now made to FIG. 16, which is a simplified pictorial illustration of an example of an intraocular lens assembly prepared by employing the apparatus of FIG. 1. As shown in FIG. 16, loop 202 of intraocular lens 200 is fastened to unstretched elongate stretchable loop extension element 112 within connector 122 and loop 204 of intraocular lens 200 is fastened to unstretched elongate stretchable loop extension element 114 within connector 124.

It is appreciated that in the orientation of FIG. 16, intraocular lens 200 along with loops 202 and 204 is in an inverted configuration relative to the configuration of FIGS. 1A-15. In the configuration of FIG. 16, loop 202 serves as a leading left-hand loop when implanting intraocular lens 200 into an eye of a patient, as will be described hereinbelow with reference to FIGS. 18-25.

Figure 17A:
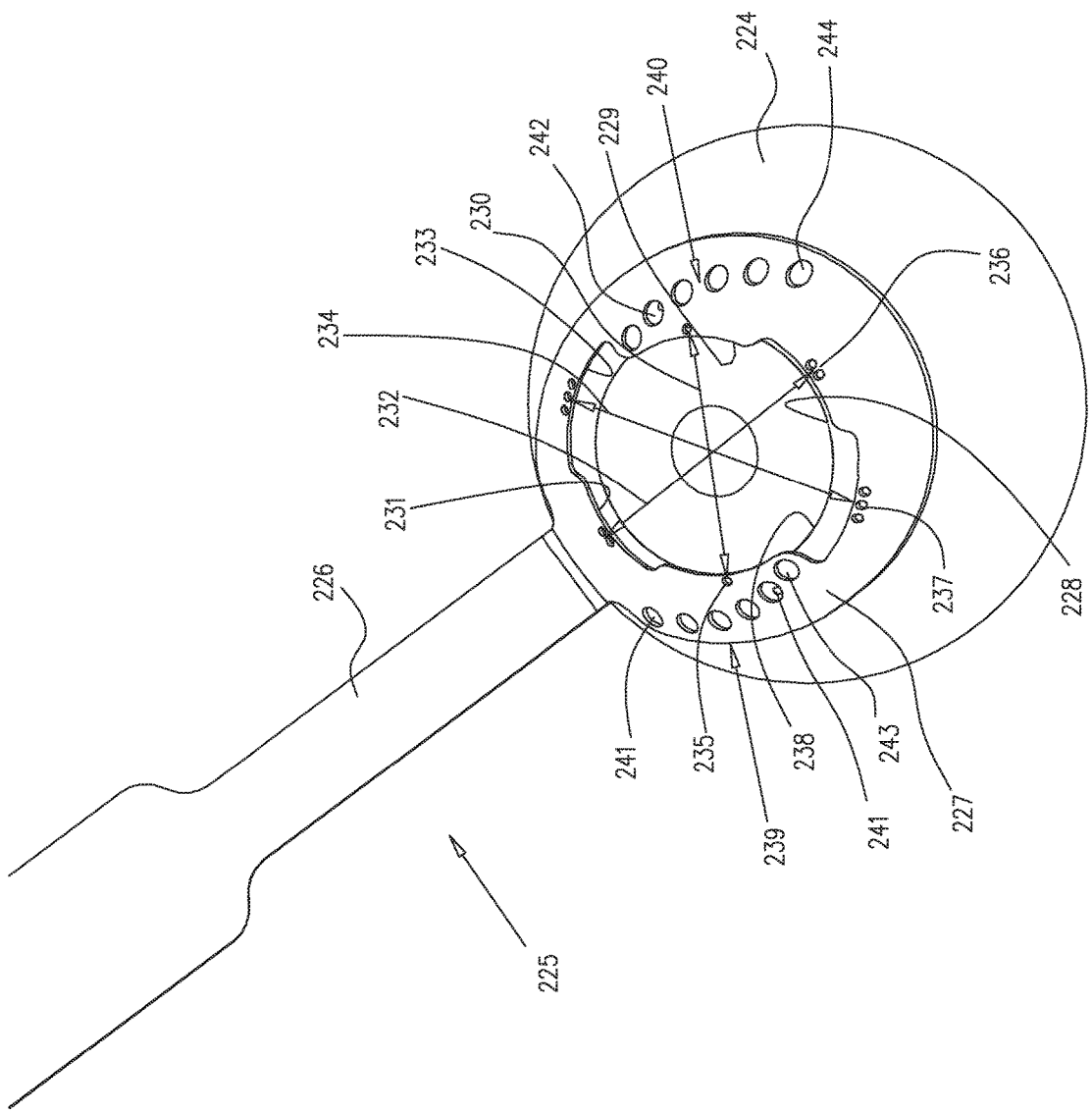
FIG. 17A is a simplified pictorial illustration of a sclera scale ruler (SSR) device for guiding a surgeon in forming a pair of sclerectomies in an eye of a patient, constructed in accordance with a preferred embodiment of the present invention.
Figure 17C:
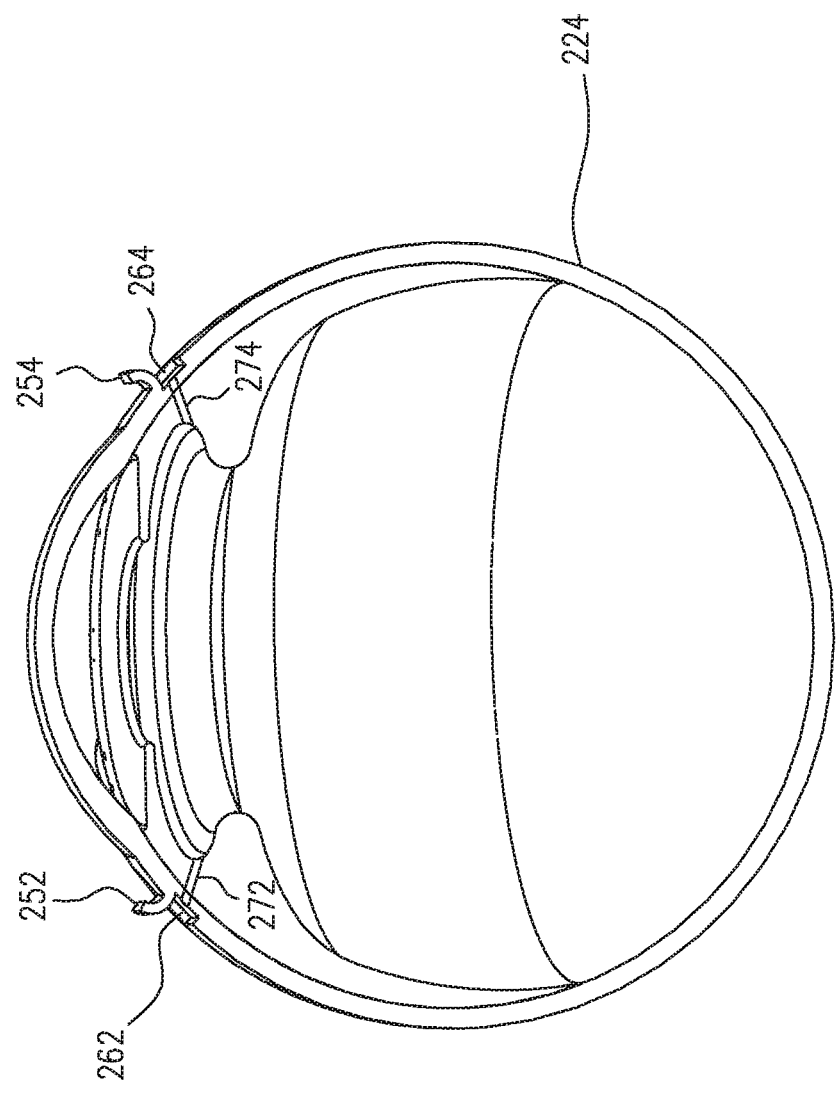
Figure 19:
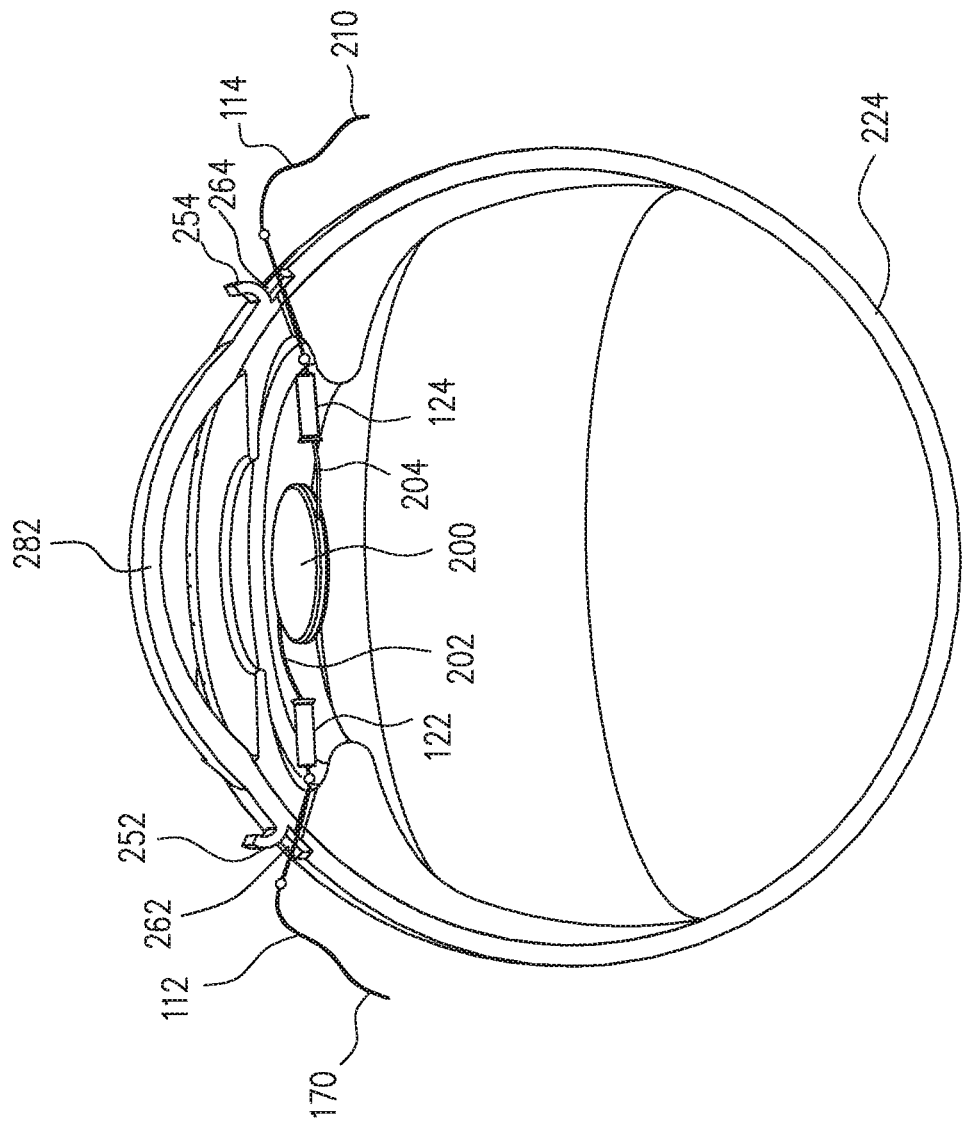
FIG. 19 is a simplified pictorial illustration of a second step in the implanting of an intraocular lens which is part of the intraocular lens assembly of FIG. 16 into an eye of a patient.

Reference is now made to FIG. 17A, which is a simplified pictorial illustration of a sclera scale ruler (SSR) device for guiding a surgeon in forming a pair of sclerectomies in an eye of a patient, constructed in accordance with a preferred embodiment of the present invention. Reference is also made to FIGS. 17B, 17C and 17D, which are simplified pictorial illustrations of an eye of a patient prepared for insertion of an intraocular lens which is part of the intraocular lens assembly of FIG. 16, via a pair of sclerectomies formed in the eye.

As shown in FIG. 17A, an SSR device is preferably employed to select optimal positions for surgically forming a pair of sclerectomies in the sclera 224 of the eye of the patient, via which sclerectomies loop extension elements 112 and 114 will be pulled through upon implantation of intraocular lens 200 within the sulcus of the eye.

It is appreciated that for optimal placement of intraocular lens 200 within the sulcus of the eye, the pair of sclerectomies through which loop extension elements 112 and 114 are pulled need to be formed symmetrically in sclera 224, 180° apart relative to the center of the limbus, and at an equal distance therefrom. This particular positioning of the sclerectomies provides for generally equal tension in both of loop extension elements 112 and 114 which thereby provides for stable implantation of intraocular lens 200 within the sulcus of the eye. It is further appreciated that the diameter of the limbus of the human eye varies among different individuals, thereby necessitating individual measurement and placement of the sclerectomies for each individual patient. The diameter of the limbus typically ranges between 11 and 13 millimeters. The preferred diameter between the pair of sclerectomies is typically at least 0.5 millimeters wider than the diameter of the limbus, although it is appreciated that the SSR device may be configured for other ranges of diameters.

SSR device 225 illustrated in FIG. 17A preferably includes a handle portion 226 and a spherical cap portion 227. A multi-diameter generally circular cutout 228 is preferably formed in spherical cap portion 227. Multi-diameter generally circular cutout 228 is preferably formed with a first portion 229 having a first diameter 230, a second portion 231 having a second diameter 232, wider than first diameter 230, and a third portion 233 having a third diameter 234, wider than second diameter 232. First, second and third diameters 230, 232 and 234 are preferably of 11, 12 and 13 millimeters in length respectively, however other suitable diameters may be employed. It is appreciated that in alternative embodiments, multi-diameter generally circular cutout 228 may comprise any number of portions having varying diameters. It is further appreciated that in yet another alternative embodiment, a single-diameter cutout may be employed.

As further shown in FIG. 17A, also preferably formed in spherical cap portion 227, in close proximity to cutout 228, are a pair of single positioning indicators 235 formed on the edge of first portion 229 of cutout 228, a pair of double positioning indicators 236 formed on the edge of second portion 231 of cutout 228, and a pair of triple positioning indicators 237 formed on the edge of third portion 233 of cutout 228.

It is a particular feature of this embodiment of the present invention that an operator of SSR device 225 may utilize positioning indicators 235, 236 and 237 to position SSR device 225 so that the limbus 238 of the eye is centered within at least one of first, second and third portions 229, 231 and 233 of cutout 228, and to thereby estimate the diameter of the limbus 238 to be the diameter of which of portions 229, 231 and 233 most closely centering limbus 238 therewithin.

As yet further shown in FIG. 17A, also preferably formed in spherical cap portion 227 are two corresponding series 239 and 240 of sclerectomy guiding apertures formed about cutout 228, each sclerectomy guiding aperture in series 239 having a corresponding paired sclerectomy guiding aperture in series 240 positioned 180° apart therefrom relative to the center of cutout 228, and at an equal distance therefrom. As clearly shown in FIG. 17A, paired sclerectomy guiding apertures of series 239 and 240 are formed at progressively wider diameters about first, second and third portions 229, 231 and 233 of cutout 228. For example, paired sclerectomy guiding apertures 241 and 242 of respective series 239 and 240 may be formed with a diameter which is 0.5 millimeters wider than first diameter 230, and paired sclerectomy guiding apertures 243 and 244 of respective series 239 and 240 may be formed with a diameter which is 3 millimeters wider than third diameter 234.

It is therefore another particular feature of this embodiment of the present invention that series 239 and 240 of sclerectomy guiding apertures provide the operator of SSR device 225 with a plurality of sclerectomy guiding apertures, each formed at one of a relatively wide and discrete range of diameters about first, second and third portions 229, 231 and 233 of cutout 228. This, in turn, enables the operator of SSR device 225, upon centering limbus 238 within cutout 228 and estimating the diameter of limbus 238 as described hereinabove, to select a pair of sclerectomy guiding apertures of series 239 and 240 defining a diameter which is wider than that of limbus 238 and which is most suitable for surgically forming a pair of sclerectomies at corresponding positions on sclera 224.

Upon selecting the most suitable pair of sclerectomy guiding apertures, the operator of device 225 may surgically form the pair of sclerectomies via the selected sclerectomy guiding apertures, or alternatively, may employ the selected sclerectomy guiding apertures to mark corresponding positions on sclera 224 and upon removing device 225 may surgically form a pair of sclera flaps about the marked positions and then form a corresponding pair of sclerectomies within recesses formed by the flaps.

In the example of FIG. 17A, the operator of SSR device 225 employed SSR device 225 to surgically form sclerectomies 241 and 242 on sclera 224.

In the example of FIG. 17B, the operator of SSR device 225 employed SSR device 225 to first mark selected sclerectomies positions on sclera 224, and upon removal SSR device 225 from the eye then surgically formed a pair of scleral flaps 252 and 254 about the marked positions, thereby forming corresponding recesses 262 and 264. Sclerectomies 272 and 274 which communicate between corresponding recesses 262 and 264 and the interior of sclera 224 are then surgically formed, as further illustrated in FIGS. 17C and 17D.

It is appreciated that, alternatively, a virtual image of cutout 228 may be projected onto the patient's eye, wherein the projected image of cutout 228 includes all the elements of cutout 228 described hereinabove with regard to FIGS. 17A & 17B, thereby obviating the need for physical SSR device 225.

As described hereinabove, the novel procedure described hereinbelow in which intraocular lens 200 will be placed within the sulcus and fixed to the sclera is particularly suitable for pseudophakic patients for whom the capsular bag is not intact, for example as a result of cataract surgery or lens exchange. It is appreciated that the novel procedure described hereinbelow is also suitable for any surgical procedure which involves implantation of intraocular devices such as, for example, an artificial iris or an intraocular telescopic lens.

Reference is now made to FIGS. 18, 19, 20, 21, 22A, 22B, 23, 24 and 25, which are simplified pictorial illustrations of steps in the implantation of an intraocular lens which is part of the intraocular lens assembly of FIG. 16 into an eye of a patient.

As shown in the first step of FIG. 18, loose ends 170 and 210 of corresponding stretchable loop extension elements 112 and 114 are inserted into the eye via a limbal cut 280 surgically formed between the cornea 282 and the sclera 224, and are pulled through sclerectomies 272 and 274, respectively, by intraocular forceps. Intraocular lens 200 is then inserted through limbal cut 280 to the position shown in FIG. 19.

Figure 20:
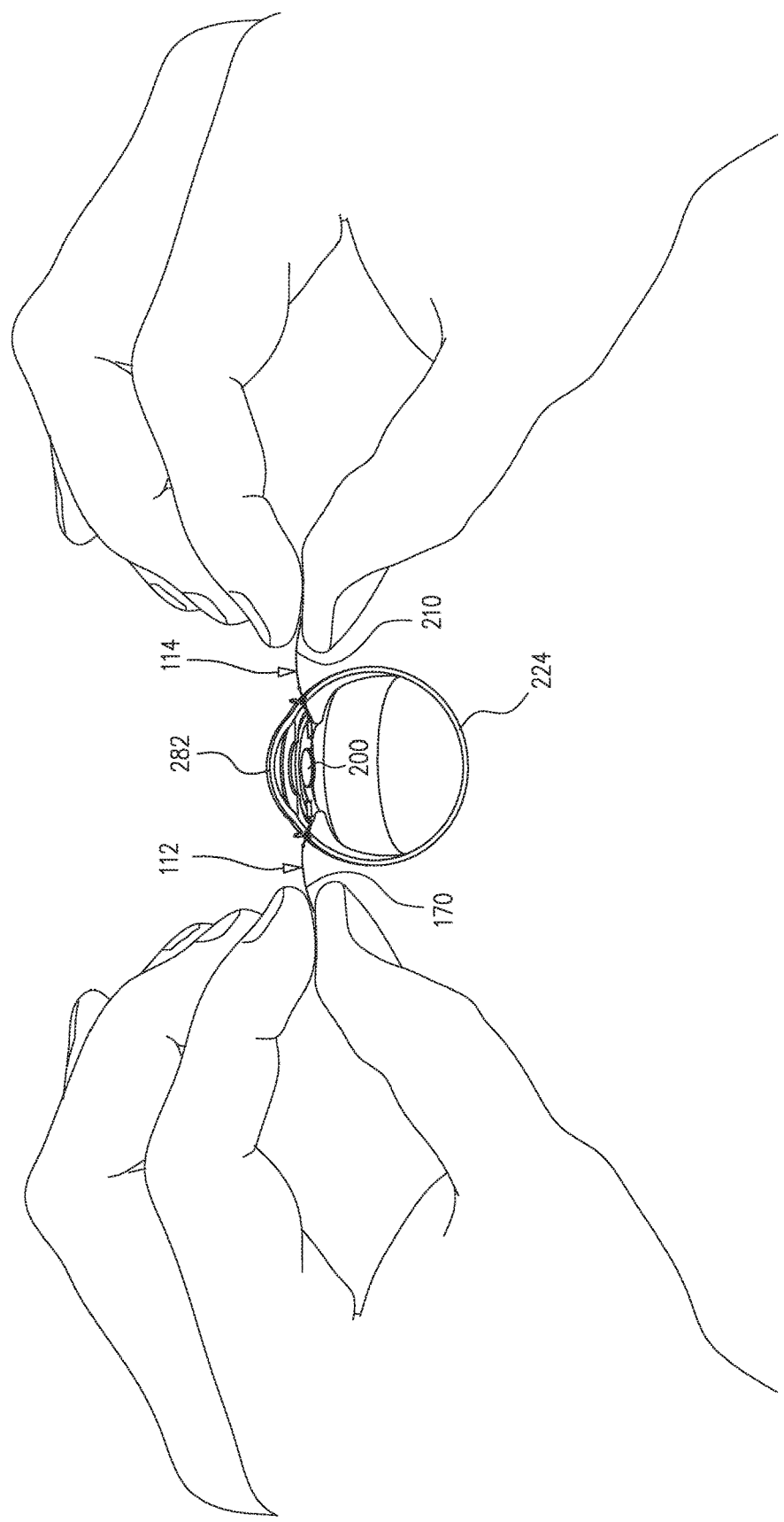
FIG. 20 is a simplified pictorial illustration of a third step in the implanting of an intraocular lens which is part of the intraocular lens assembly of FIG. 16 into an eye of a patient.

Thereafter, as shown in FIG. 20, loose ends 170 and 210 of corresponding stretchable loop extension elements 112 and 114 are further completely pulled through sclerectomies 272 and 274, respectively, thereby pulling respective connectors 122 and 124 along with loops 202 and 204 from within sclera 224 through sclerectomies 272 and 274, respectively.

It is a particular feature of the present invention that once pulled through sclerectomies 272 and 274, connectors 122 and 124 are operative to serve as motion-limiting elements which prevent loops 202 and 204, corresponding connectors 122 and 124 and corresponding stretchable loop extension elements 112 and 114 from being retracted into sclera 224.

Figure 21:
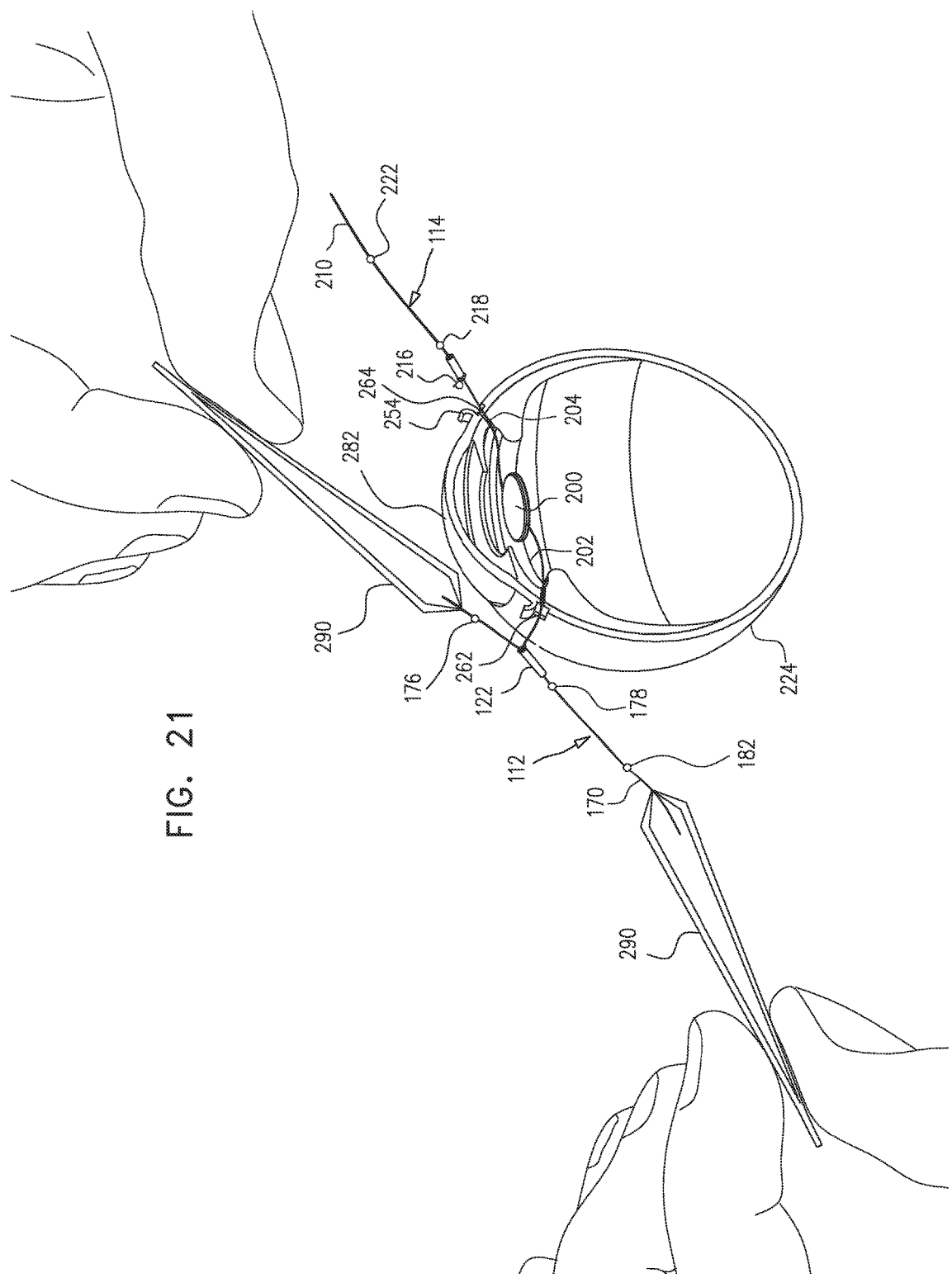
FIG. 21 is a simplified pictorial illustration of a fourth step in the implanting of an intraocular lens which is part of the intraocular lens assembly of FIG. 16 into an eye of a patient.

As further shown in FIG. 21, forceps 290 are employed at a point distal to connector motion-limiting element 176 and at a point distal to extension element retaining element 182 to stretch stretchable loop extension element 112 and to thereby release loop 202 from connector 122. As described hereinabove, in the stretched configuration, the diameter of elongate stretchable loop extension element 112 is narrower than the diameter of cylindrical bore 152, thereby releasing elongate stretchable loop extension element 112 from inner surface 174 of cylindrical bore 152 and thereby allowing for release of loop 202 from connector 122. As further described hereinabove, once pulled through sclerectomy 274, connector 124 is operative to serve as a motion-limiting element which prevents loop 204, connector 124 and stretchable loop extension element 114 from being retracted into sclera 224 while releasing loop 202 from connector 122. After releasing loop 202 from connector 122, loop 202 is then fixated into a bore 296 formed in a side surface of recess 262.

Similarly, as further shown in FIG. 22A, forceps 290 are employed at a point distal to connector motion-limiting element 216 and at a point distal to extension element retaining element 222 to stretch stretchable loop extension element 114 and to thereby release loop 204 from connector 124. As described hereinabove, in the stretched configuration, the diameter of elongate stretchable loop extension element 114 is narrower than the diameter of cylindrical bore 154, thereby releasing elongate stretchable loop extension element 114 from inner surface 214 of cylindrical bore 154 and thereby allowing for release of loop 204 from connector 124 and fixation of loop 204 into a bore 298 formed in a side surface of recess 264. Released elongate stretchable loop extension element 114 is shown in FIG. 22B.

Figure 23:
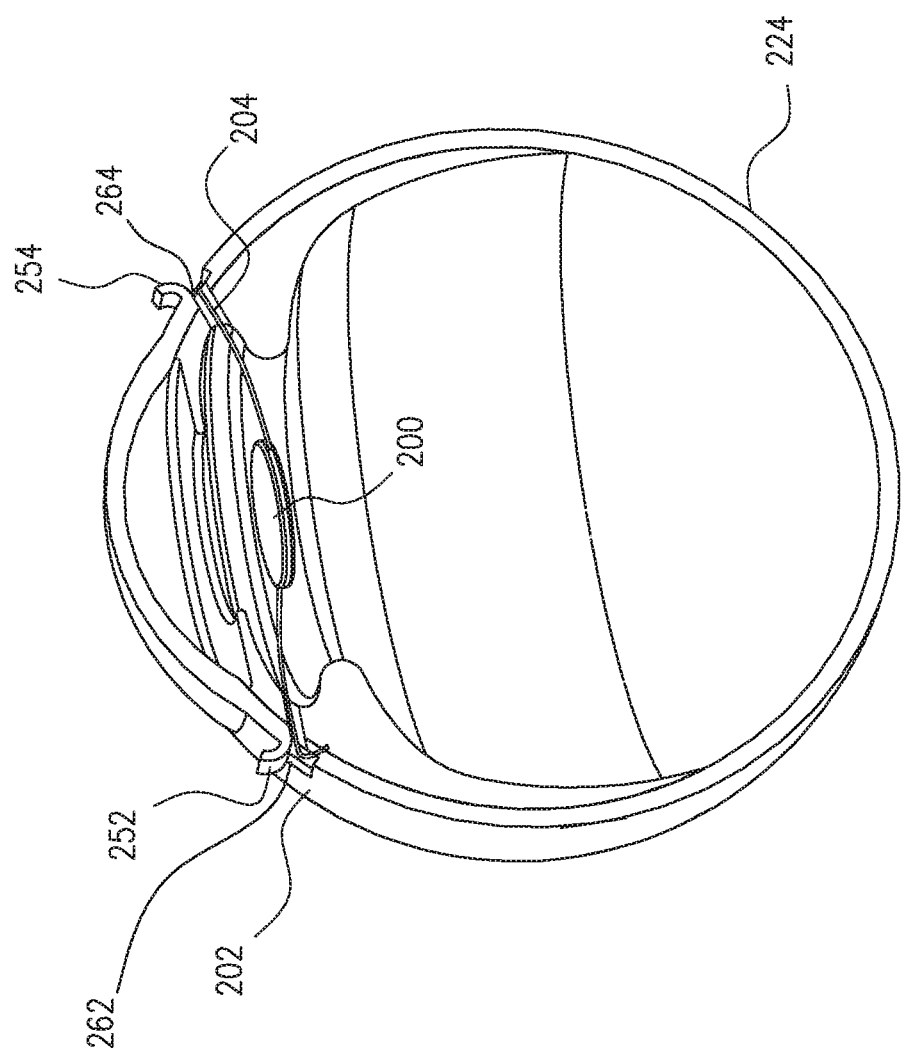
FIG. 23 is a simplified pictorial illustration of a sixth step in the implanting of an intraocular lens which is part of the intraocular lens assembly of FIG. 16 into an eye of a patient.

As shown in FIG. 23, loops 202 and 204 remain protruding through respective sclerectomies 272 and 274 and fixated into bores 296 and 298 formed in side surfaces of corresponding recesses 262 and 264, as described hereinabove with regard to FIGS. 21 and 22B.

Figure 24:
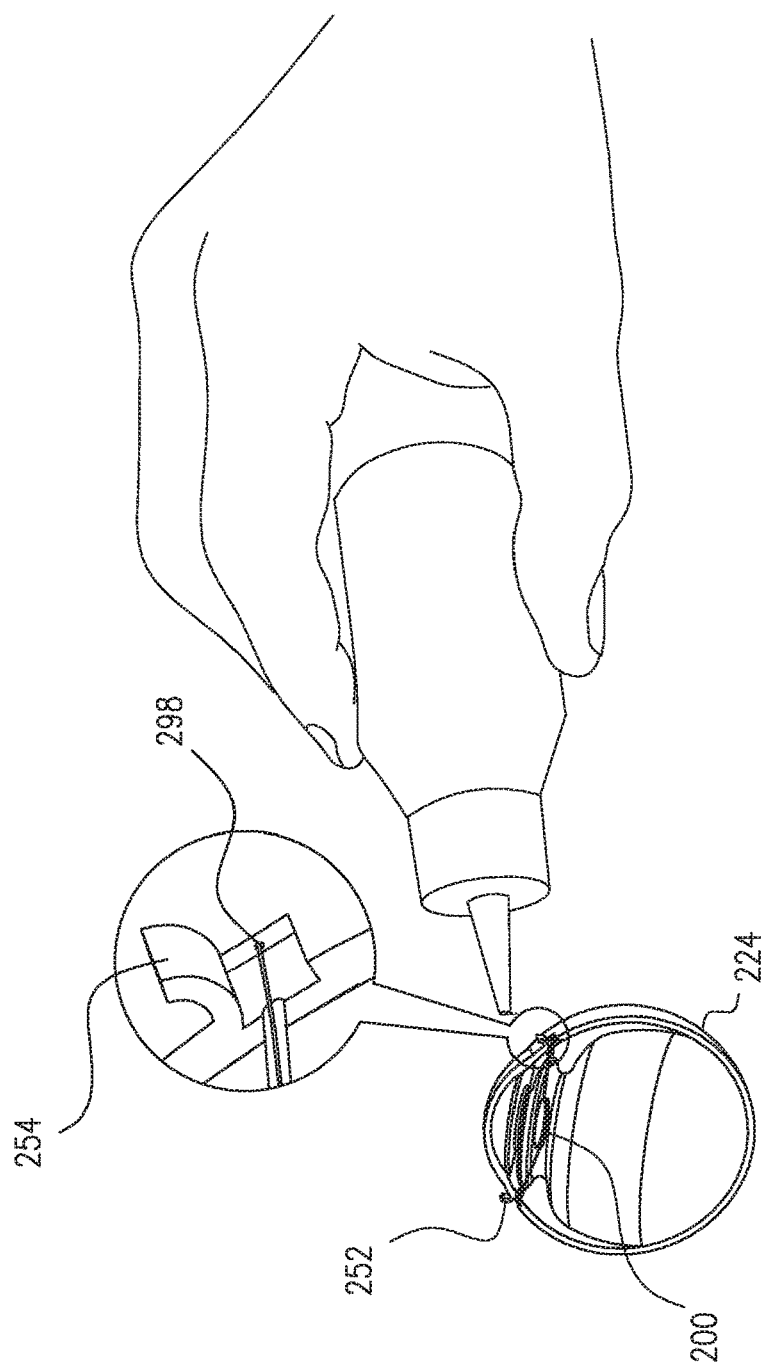
FIG. 24 is a simplified pictorial illustration of a seventh step in the implanting of an intraocular lens which is part of the intraocular lens assembly of FIG. 16 into an eye of a patient.
Figure 25:
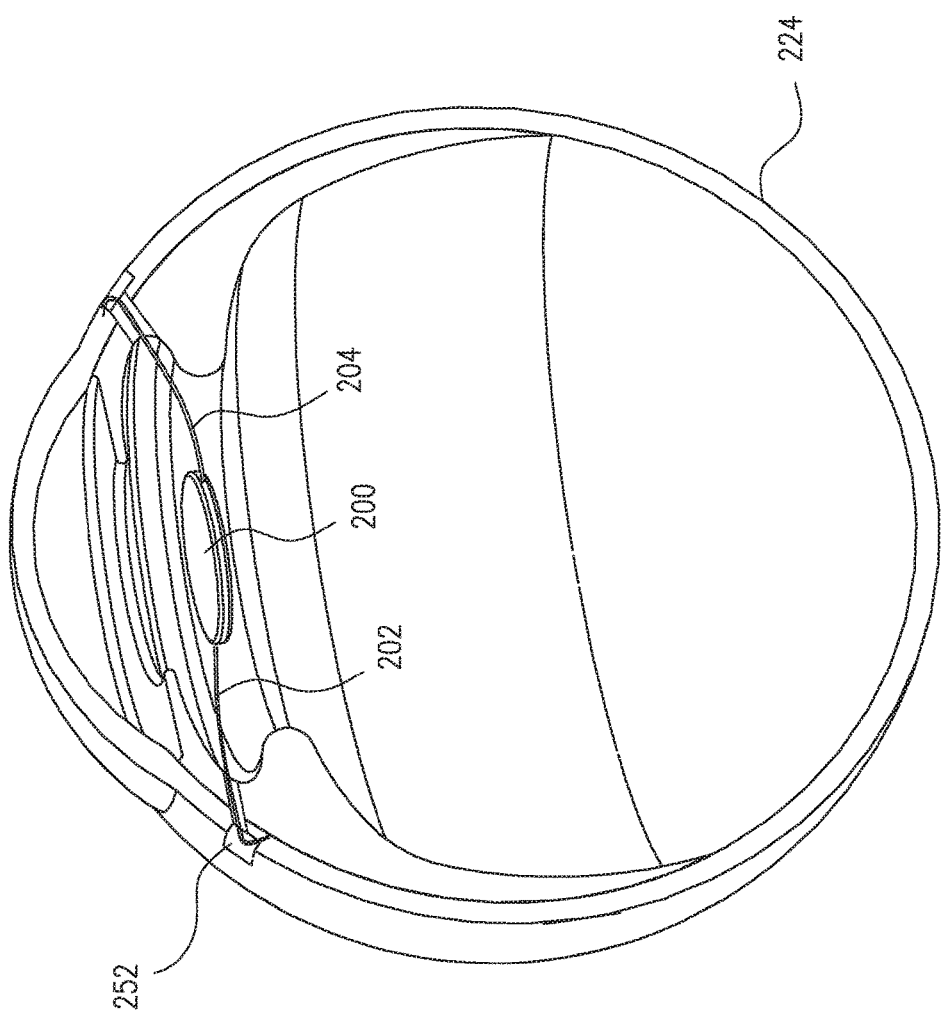
FIG. 25 is a simplified pictorial illustration of an eighth step in the implanting of an intraocular lens which is part of the intraocular lens assembly of FIG. 16 into an eye of a patient.

Turning now to FIG. 24, it is shown that after loose ends of loops 202 and 204 are inserted into corresponding bores 296 and 298, surgical glue is applied to a bottom surface of each of recesses 262 and 264. Thereafter, as shown in FIG. 25, scleral flaps 252 and 254 are folded back into respective recesses 262 and 264, thereby gluing flaps 252 and 254 into corresponding recesses 262 and 264 and thereby forming a smooth surface of sclera 224.

It will be appreciated by persons skilled in the art that the present invention is not limited by what has been particularly shown and described hereinabove. Rather the scope of the present invention includes both combinations and subcombinations of the various features described hereinabove as well as modifications thereof which would occur to persons skilled in the art upon reading the foregoing description and which are not in the prior art.

The invention claimed is:

1. Apparatus for guiding surgical formation of a pair of symmetrical sclerectomies in an eye of a patient, said apparatus comprising:
    a spherical cap portion, said spherical cap portion comprising a multi-diameter generally circular cutout portion formed therewithin, said multi-diameter generally circular cutout portion comprising at least a first portion having a first diameter and a second portion having a second diameter, said multi-diameter generally circular cutout portion being arranged for placement over the limbus of said eye and for centering said limbus within at least one of said at least first and second portions, thereby enabling estimating the diameter of said limbus to be approximately equal to the diameter of said at least one of said at least first and second portions centering said limbus therewithin; and
    at least first and second series of sclerectomy guiding apertures formed about said cutout portion, each first sclerectomy guiding aperture of said first series having a paired second sclerectomy guiding aperture in said second series formed 180° apart from said first sclerectomy guiding aperture relative to a center of said cutout portion;
    said at least first and second series of sclerectomy guiding apertures together comprising at least one pair of corresponding first and second sclerectomy guiding apertures having a diameter therebetween which is wider than the diameter of at least one of said first and second portions.

2. Apparatus for guiding surgical formation of a pair of symmetrical sclerectomies in an eye of a patient according to claim 1 and wherein said at least one pair of corresponding first and second sclerectomy guiding apertures is arranged for guiding surgical formation of a pair of symmetrical sclerectomies in the sclera of an eye of a patient.

3. Apparatus for guiding surgical formation of a pair of symmetrical sclerectomies in an eye of a patient according to claim 1 and wherein each said first sclerectomy guiding aperture of said first series and said paired second sclerectomy guiding aperture of said second series are formed at equal distances from said cutout portion.

4. Apparatus for guiding surgical formation of a pair of symmetrical sclerectomies in an eye of a patient according to claim 1 and wherein said first sclerectomy guiding apertures of said first series are formed at varying distances from said cutout portion.

5. Apparatus for guiding surgical formation of a pair of symmetrical sclerectomies in an eye of a patient according to claim 1 and wherein said second diameter is wider than said first diameter.

6. Apparatus for guiding surgical formation of a pair of symmetrical sclerectomies in an eye of a patient according to claim 1 and also comprising a handle portion.

7. Apparatus for guiding surgical formation of a pair of symmetrical sclerectomies in an eye of a patient according to claim 1 and also comprising at least a pair of single positioning indicators formed on an edge of said first portion and a pair of double positioning indicators formed on an edge of said second portion, said positioning indicators indicating, to an operator of said apparatus, the position of said first and second portions.

8. Apparatus for guiding surgical formation of a pair of symmetrical sclerectomies in an eye of a patient according to claim 1 and wherein said multi-diameter generally circular cutout portion also comprises a third portion having a third diameter, said at least first and second series of sclerectomy guiding apertures together comprising at least one pair of corresponding first and second sclerectomy guiding apertures having a diameter therebetween which is wider than the diameter of said third portion.

9. Apparatus for guiding surgical formation of a pair of symmetrical sclerectomies in an eye of a patient according to claim 8 and wherein said third diameter is wider than said second diameter.

10. Apparatus for guiding surgical formation of a pair of symmetrical sclerectomies in an eye of a patient according to claim 8 and also comprising a pair of triple positioning indicators formed on an edge of said third portion.

11. A method for guiding surgical formation of a pair of symmetrical sclerectomies in an eye of a patient, said method comprising:
placing a spherical cap portion over the limbus of said eye and centering said limbus therewithin, said spherical cap portion comprising a multi-diameter generally circular cutout, said cutout comprising at least a first portion having a first diameter and a second portion having a second diameter;
estimating the diameter of said limbus to be approximately equal to the diameter of at least one of at least first and second portions of said cutout; and
selecting at least one pair of first and second sclerectomy guiding apertures for guiding surgical formation of a pair of symmetrical sclerectomies in the sclera of an eye of a patient, said at least one pair of first and second sclerectomy guiding apertures being formed about said cutout 180° thereapart relative to a center of said cutout and having a diameter therebetween which is wider than the diameter of at least one of said first and second portions.

12. A method for guiding surgical formation of a pair of symmetrical sclerectomies in an eye of a patient according to claim 11 and wherein each of said at least one pair of first and second sclerectomy guiding apertures are formed at equal distances from said cutout.

13. A method for guiding surgical formation of a pair of symmetrical sclerectomies in an eye of a patient according to claim 11 and wherein said second diameter is wider than said first diameter.

14. A method for guiding surgical formation of a pair of symmetrical sclerectomies in an eye of a patient according to claim 11 and also comprising employing at least a pair of single positioning indicators formed on an edge of said first portion and a pair of double positioning indicators formed on an edge of said second portion, said positioning indicators being operative to indicate the position of said first and second portions.

15. Apparatus for guiding surgical formation of a pair of symmetrical sclerectomies in an eye of a patient, said apparatus comprising:
a spherical cap portion, said spherical cap portion comprising a generally circular cutout portion formed therewithin, said generally circular cutout portion being arranged for placement over the limbus of said eye and for centering said limbus therewithin, thereby enabling estimating the diameter of said limbus to be approximately equal to the diameter of said generally circular cutout portion centering said limbus therewithin; and
at least first and second series of sclerectomy guiding apertures formed about said cutout portion, each first sclerectomy guiding aperture of said first series having a paired second sclerectomy guiding aperture in said second series formed 180° apart from said first sclerectomy guiding aperture relative to a center of said cutout portion;
said at least first and second series of sclerectomy guiding apertures together comprising at least one pair of corresponding first and second sclerectomy guiding apertures having a distance therebetween which is wider than said diameter of said generally circular cutout portion.

16. Apparatus for guiding surgical formation of a pair of symmetrical sclerectomies in an eye of a patient according to claim 15 and wherein said at least one pair of corresponding first and second sclerectomy guiding apertures is arranged for guiding surgical formation of a pair of symmetrical sclerectomies in the sclera of an eye of a patient.

17. Apparatus for guiding surgical formation of a pair of symmetrical sclerectomies in an eye of a patient according to claim 15 and wherein each said first sclerectomy guiding aperture of said first series and said paired second sclerectomy guiding aperture of said second series are formed at equal distances from said cutout portion.

18. Apparatus for guiding surgical formation of a pair of symmetrical sclerectomies in an eye of a patient according to claim 15 and wherein said first sclerectomy guiding apertures of said first series are formed at varying distances from said cutout portion.

19. Apparatus for guiding surgical formation of a pair of symmetrical sclerectomies in an eye of a patient according to claim 15 and also comprising a handle portion.

20. A method for guiding surgical formation of a pair of symmetrical sclerectomies in an eye of a patient, said method comprising:
placing a spherical cap portion over the limbus of said eye and centering said limbus therewithin, said spherical cap portion comprising a generally circular cutout;
estimating the diameter of said limbus to be approximately equal to the diameter of said generally circular cutout; and
selecting at least one pair of first and second sclerectomy guiding apertures for guiding surgical formation of a pair of symmetrical sclerectomies in the sclera of an eye of a patient, said at least one pair of first and second sclerectomy guiding apertures being formed about said cutout 180° thereapart relative to a center of said cutout and having a diameter therebetween which is wider than said diameter of said generally circular cutout.

21. A method for guiding surgical formation of a pair of symmetrical sclerectomies in an eye of a patient according to claim 20 and wherein each of said at least one pair of first and second sclerectomy guiding apertures are formed at equal distances from said cutout.

* * * * *